(12) United States Patent
Gaul et al.

(10) Patent No.: US 9,034,852 B2
(45) Date of Patent: *May 19, 2015

(54) SUBSTITUTED PHENOXY N-ALKYLATED THIAZOLIDINEDIONES AS ESTROGEN RELATED RECEPTOR-α MODULATORS

(75) Inventors: Michael Gaul, Yardley, PA (US); Lily Lee Searle, Waltham, MA (US); Dionisios Rentzeperis, Downingtown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 274 days.

This patent is subject to a terminal disclaimer.

(21) Appl. No.: 13/346,808

(22) Filed: Jan. 10, 2012

(65) Prior Publication Data

US 2012/0108571 A1  May 3, 2012

Related U.S. Application Data

(62) Division of application No. 12/043,291, filed on Mar. 6, 2008, now Pat. No. 8,119,669.

(60) Provisional application No. 60/893,458, filed on Mar. 7, 2007.

(51) Int. Cl.
*C07D 277/34* (2006.01)
*C07D 417/06* (2006.01)

(52) U.S. Cl.
CPC ............ *C07D 277/34* (2013.01); *C07D 417/06* (2013.01)

(58) Field of Classification Search
CPC ............................ C07D 277/34; C07D 417/06
See application file for complete search history.

(56) References Cited

U.S. PATENT DOCUMENTS

| 6,518,268 | B1 | 2/2003 | Chin et al. |
| 2006/0014812 | A1 | 1/2006 | Player et al. |

FOREIGN PATENT DOCUMENTS

| EP | 0537300 B1 | 4/1995 |
| EP | 1398029 A1 | 3/2004 |
| WO | WO 01/78721 A1 | 10/2001 |
| WO | WO 03/008635 A2 | 1/2003 |
| WO | WO 2004/024061 A2 | 3/2004 |
| WO | WO 06/004555 A1 | 1/2006 |
| WO | WO 2006/047269 A2 | 5/2006 |

OTHER PUBLICATIONS

Mayo Clinic. "Prediabetes." © 2014. Available from: < http://www.mayoclinic.org/diseases-conditions/prediabetes/basics/treatment/con-20024420?p=1 >.*

"How to prevent type 2 diabetes", http://diabetes.webmd.com/guide/preventing-type-2-diabetes, accessed Nov. 2, 2010.

Aranda et al., "Nuclear Hormone Receptors and Gene Expression.", Physiol. Rev., 2001, pp. 1269-1304, vol. 81(3).
Ariazi et al., "Estrogen-related Receptor α and Estrogen-related Receptor γ Associate with Unfavorable and Favorable Biomarkers, Respectively, in Human Breast Cancer 1.", Cancer Res., 2002, pp. 6510-6518, vol. 62.
Berge et al., "Pharmaceutical Salts.", J. Pharm.Sci., 1977, pp. 1-19, vol. 66(1).
Bonnelye et al., "Estrogen Receptor-Related Receptor α Impinges on the Estrogen Axis in Bone: Potential Function in Osteoporosis.", Endocrinology, 2002, pp. 3658-3670, vol. 143(9).
Bonnelye et al., "The ERR-1 Orphan Receptor Is a Transcriptional Activator Expressed During Bone Development.", Mol. Endocrin, 1997, pp. 905-916, vol. 11.
Bonnelye, et al., "The Orphan Nuclear Estrogen Receptor—related Receptor α (ERRα) Is Expressed throughout Osteoblast Differentiation and Regulates Bone Formation in Vitro.", J. Cell Biol. 2001, pp. 971-984, vol. 153.
Giguere et al., "Identification of a new class of steroid hormone receptors.", Nature, 1988, pp. 91-94, vol. 331.
Giguere, V., "Orphan Nuclear Receptors: From Gene to Function.", Endocrine Rev., 1999, pp. 689-725, vol. 20(5).
Giguere, V., "To ERR in the estrogen pathway.", Trends in Endocrinol. Metab., 2002, pp. 220-225, vol. 13.

(Continued)

*Primary Examiner* — Andrew D Kosar
*Assistant Examiner* — John S Kenyon
(74) *Attorney, Agent, or Firm* — Jeremy K. McKown

(57) ABSTRACT

The present invention relates to compounds of Formula (I),

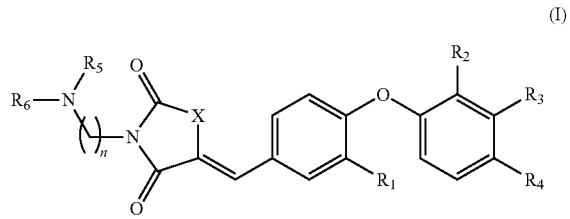

methods for preparing these compounds, compositions, intermediates and derivatives thereof and for treating a condition including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

4 Claims, No Drawings

(56) References Cited

OTHER PUBLICATIONS

Grundy et al., "Definition of Metabolic Syndrome: Report of the National Heart, Lung, and Blood Institute/American Heart Association Conference on Scientific Issues Related to Definition.", Circulation, 2004, pp. 433-438, vol. 109(3).
Handschin et al., Drug Discover Today Therapeutic Targets, 2005, pp. 151-156, vol. 2(2).
Hong et al., "Hormone-independent Transcriptional Activation and Coactivator Binding by Novel Orphan Nuclear Receptor ERR3.", J. Biol. Chem. 1999, pp. 22618-22626, vol. 274.
Jantzen and Robinson. Modern Pharmaceutics, 1996, p. 596.
Jones, P.L. And Y.B. Shi., "N-CoR-HDAC Corepressor Complexes: Roles in Transcriptional Regulation by Nuclear Hormone Receptors.", Curr. Top. Microbiol. Immunol., 2003, pp. 237-268, vol. 274.
Kamei et al., "PPARγ coactivator 1β ERR ligand 1 is an ERR protein ligand, whose expression induces a high-energy expenditure and antagonizes obesity.", Proc. Natl. Acad. Sci., 2003, pp. 12378-12383, 100(21), USA.
Korach, K. S., "Insights from the Study of Animals Lacking Functional Estrogen Receptor.", Science, Jan. 1994, pp. 1524-1527, vol. 266.
Kraus et al., "Estrogen-related Receptor α1 Actively Antagonizes Estrogen Receptor-regulated Transcription in MCF-7 Mammary Cells.", J. Biol. Chem., 2002, pp. 24826-24834, vol. 272.
Luo et al., "Reduced Fat Mass in Mice Lacking Orphan Nuclear Receptor Estrogen-Related Receptor α.", Mol. Cell. Biol., 2003, pp. 7947-7956, vol. 23(22).
McKenna et al., "Nuclear Receptor Coregulators: Cellular and Molecular Biology.", Endocrine Rev., 1999, pp. 321-344, vol. 20.
Mootha et al., "Errα and Gabpa/b specify PGC-1α-dependent oxidative phosphorylation gene expression that is altered in diabetic muscle.", Proc. Natl. Acad. Sci., Apr. 27, 2004, pp. 6570-6575, vol. 101(17).
Olefsky, J.M., "Minireview Prologue. Nuclear Receptor Minireview Series.", J. Biol. Chem., 2001, pp. 36863-36864, vol. 276(40).
Pacifici, R.J., "Estrogen, Cytokines, and Pathogenesis of Postmenopausal Osteoporosis.", Bone Miner. Res., 1996, pp. 1043-1051, vol. 11(8).
Rochette-Egly et al., "Retinoic Acid Receptor β: Immunodetection and Phosphorylation on Tyrosine Residues.", Mol. Endocrinol., 1992, pp. 2197-2209, vol. 6.
Rochette-Egly et al., "Stimulation of RARa Activation Function AF-1 through Binding to the General Transcription Factor TFIIH and Phosphorylation by CDK7.", Cell, 1997, pp. 97-107, vol. 90.
Schreiber et al., PNAS, 2004, pp. 6472-6477, vol. 101(17).
Sladek et al., "The Orphan Nuclear Receptor Estrogen-Related Receptor α Is a Transcriptional Regulator of the Human Medium-Chain Acyl Coenzyme a Dehydrogenase Gene.", Mol. Cell. Biol. 1997, pp. 5400-5409, vol. 17.
Strum, Jay C. et al., "Rosiglitazone Induces Mitochondrial Biogenesis in Mouse Brain". Journal of Alzheimer's Disease, Mar. 1, 2007, pp. 45-51, vol. 11(1), IOS Press, Amsterdam, NL., XP009089920.
Sumi, D. And L.J. Ignarro, "Estrogen-related receptor α1 up-regulates endothelial nitric oxide synthase expression.", Proc Natl. Acad. Sci. 2003, pp. 14451-14456, vol. 100.
Turner et al., "Skeletal Effects of Estrogen.", Endocrine Rev. 1994, pp. 275-300, vol. 15(3).
Vanacker et al., "Transcriptional targets shared by estrogen receptor-related receptors (ERRs) and estrogen receptor (ER) α, but not by ERβ.", The EMBO Journal, 1999, pp. 4270-4279, vol. 18.
Vega, R.B. and D.P. Kelly, "A Role for Estrogen-related Receptor α in the Control of Mitochondrial Fatty Acid β-Oxidation during Brown Adipocyte Differentiation.", J. Biol. Chem. 1997, pp. 31693-31699, vol. 272.
Willy et al., "Regulation of PPARγ coactivator 1α (PGC-1α) signaling by an estrogen-related receptor α (ERRα) ligand.", Proc. Natl. Acad. Sci., Jun. 15, 2004, pp. 8912-8917, vol. 101(24).
Windahl et al., "Increased cortical bone mineral content but unchanged trabecular bone mineral density in female ERβ—/—mice.", J. Clin. Invest., 1999, pp. 895-901, vol. 104(7).
Wurtz et al., "A canonical structure for ligand-binding domain of nuclear receptors.", Nat. Struct. Biol., 1996, pp. 87-94, vol. 3.
Xu et al., "Structural basis for antagonist mediated recruitment of nuclear co-repressors by PPARa.", Nature 2002, pp. 813-817, vol. 415 (6873).
Zhang, Z. And C.T. TENG, "Estrogen Receptor-related Receptor α1 Interacts with Coactivator and Constitutively Activates the Estrogen Response Elements of the Human Lactoferrin Gene.", J. Biol. Chem., 2000, pp. 20837-20846, vol. 275(27).
International Search Report relating to corresponding International Patent Application No. PCT/US2008/056018. Date of mailing of International Search Report, Sep. 24, 2008.
Written Opinion of the International Searching Authority relating to corresponding International Patent Application No. PCT/US2008/056018. Date of mailing of Written Opinion, Sep. 24, 2008.

* cited by examiner

SUBSTITUTED PHENOXY N-ALKYLATED THIAZOLIDINEDIONES AS ESTROGEN RELATED RECEPTOR-α MODULATORS

CROSS REFERENCE TO RELATED APPLICATION

This application is a divisional application of U.S. Ser. No. 12/043,291 filed Mar. 6, 2008, now granted as U.S. Pat. No. 8,119,669, which claims the benefit of U.S. Provisional Application No. 60/893,458, filed Mar. 7, 2007, the disclosures of which are hereby incorporated by reference in their entireties.

FIELD OF THE INVENTION

The present invention relates to certain novel compounds, methods for preparing compounds, compositions, intermediates and derivatives thereof and for treating conditions such as cancer, arthritis, inflammatory airway disease, and metabolic disorders. More particularly, the compounds of the present invention are Estrogen Related Receptor alpha (ERR-α) modulators useful for treating, ameliorating or inhibiting the onset of disease states, disorders, and conditions mediated by ERR-α activity.

BACKGROUND OF THE INVENTION

Nuclear receptors are members of a superfamily of transcription factors. The members of this family share structural similarities and regulate a diverse set of biological effects (Olefsky, J. M. J. Biol. Chem. 2001, 276(40), 36863-36864). Ligands activate or repress these transcription factors that control genes involved in metabolism, differentiation and reproduction (Laudet, V. and H. Gronmeyer. The Nuclear Receptor Factbooks. 2002, San Diego: Academic Press). Presently, the human genome project has identified about 48 members for this family and cognate ligands have been identified for about 28 of them (Giguere, V. Endocrine Rev. 1999, 20(5), 689-725). This protein family is composed of modular structural domains that can be interchanged within the members of the family without loss of function. A typical nuclear receptor contains a hypervariable N-terminus, a conserved DNA binding domain (DBD), a hinge region, and a conserved ligand-binding domain (LBD). The function of the DBD is targeting of the receptor to specific DNA sequences (NHR response elements or NREs), and the function of the LBD is recognition of its cognate ligand. Within the sequence of the nuclear receptor there are regions involved in transcriptional activation. The AF-1 domain is situated at the N-terminus and constitutively activates transcription (Rochette-Egly, C. et al. Cell 1997, 90, 97-107; Rochette-Egly, C. et al. Mol. Endocrinol. 1992, 6, 2197-2209), while the AF-2 domain is embedded within the LBD and its transcriptional activation is ligand dependent (Wurtz, J. M. et al. Nat. Struct. Biol. 1996, 3, 87-94). Nuclear receptors can exist as monomers, homodimers or heterodimers and bind to direct or inverted nucleotide repeats (Laudet and Gronmeyer, 2002; Aranda, A. and A. Pascual. Physiol. Rev. 2001, 81(3), 1269-1304).

The members of this family exist either in an activated or repressed basal biological state. The basic mechanism of gene activation involves ligand dependent exchange of co-regulatory proteins. These co-regulatory proteins are referred to as co-activators or co-repressors (McKenna, L. J. et al. Endocrine Rev. 1999, 20, 321-344). A nuclear receptor in the repressed state is bound to its DNA response element and is associated with co-repressor proteins that recruit histone deacetylases (HDACs) (Jones, P. L. and Y. B. Shi. Curr. Top. Microbiol. Immunol. 2003, 274, 237-268). In the presence of an agonist there is an exchange of co-repressors with co-activators that in turn recruit transcription factors that assemble into an ATP dependent chromatin-remodeling complex. Histones are hyper-acetylated, causing the nucleosome to unfold, and repression is alleviated. The AF-2 domain acts as the ligand dependent molecular switch for the exchange of co-regulatory proteins. In the presence of an agonist the AF-2 domain undergoes a conformational transition and presents a surface on the LBD for interaction with co-activator proteins. In the absence of an agonist or in the presence of an antagonist the AF-2 domain presents a surface that promotes interactions with co-repressor proteins. The interaction surfaces on the LBD for both co-activators, and co-repressors overlap and provide a conserved molecular mechanism for gene activation or repression that is shared by the members of this family of transcription factors (Xu, H. E. et al. Nature 2002, 415 (6873), 813-817).

Natural ligands that modulate the biological activity of nuclear receptors have been identified for only approximately one half of known nuclear receptors. Receptors for which no natural ligand has been identified are termed "orphan receptors." The discovery of ligands or compounds that interact with an orphan receptor will accelerate the understanding of the role of the nuclear receptors in physiology and disease and facilitate the pursuit of new therapeutic approaches. A subclass of these receptors where no natural ligand has been identified is for the estrogen related receptors (ERRs).

ERR-α (also known as ERR-1), an orphan receptor, is the first of the three identified members of the estrogen receptor related subfamily of orphan nuclear receptors (ERR-α, β, γ). The ERR subfamily is closely related to the estrogen receptors (ER-α and ER-β). ERR-α and ERR-β were first isolated by a low stringency hybridization screen (Giguere, V. et al. Nature 1988, 331, 91-94) followed later with the discovery of ERR-γ (Hong, H. et al. J. Biol. Chem. 1999, 274, 22618-22626). The ERRs and ERs share sequence similarity with the highest homology observed in their DBDs, approximately 60%, and all interact with the classical DNA estrogen response element. Recent biochemical evidence suggested that the ERRs and ERs share target genes, including pS2, lactoferin, aromatase and osteopontin, and share co-regulator proteins (Giguere, V. Trends in Endocrinol. Metab. 2002, 13, 220-225; Vanacker, J. M. et al. EMBO J. 1999, 18, 4270-4279; Kraus, R. J. et al. J. Biol. Chem. 2002, 272, 24286-24834; Hong et al., 1999; Zhang, Z. and C. T. Teng. J. Biol. Chem. 2000, 275, 20387-20846). Therefore, one of the main functions of ERR is to regulate the response of estrogen responsive genes. The effect of the steroid hormone estrogen is primarily mediated in the breast, bone and endometrium. Thus, the identification of compounds that will interact with ERRs should provide a benefit for the treatment of bone related disease, breast cancer and reproduction.

ERR-α is shown to be present both in normal and breast cancer tissue (Ariazi, E. A. et al. Cancer Res. 2002, 62, 6510-6518). It has been reported that the main function of ERR-α in normal breast tissue is that of a repressor for estrogen responsive genes. In breast cancers or cell lines that are non-estrogen responsive (ER-α negative), ERR-α has been reported to be in an activated state (Ariazi et al., 2002). Therefore, compounds that will interact with ERR-α may be useful agents for the treatment of breast cancer that is ER-α negative and non-responsive to classical anti-estrogenic therapy, or may be used as an adjunct agent for anti-estrogen responsive breast cancers. These agents may act as antagonists by reducing the biological activity of ERR-α in these particular tissues.

Many post-menopausal women experience osteoporosis, a condition that is a result of the reduction of estrogen production. Reduction of estrogen levels results in an increase of bone loss (Turner, R. T. et al. Endocrine Rev. 1994, 15(3), 275-300). An anabolic effect on bone development has been observed on the administration of estrogens to postmenopausal patients with osteoporosis (Pacifici, R. J. Bone Miner. Res. 1996, 11(8), 1043-1051) but the molecular mechanism is unknown since ER-a and ER-b knock-out animals have minor skeletal defects, where the action of estrogens is typically mediated (Korach, K. S. Science 1994, 266, 1524-1527; Windahl, S. H. et al. J. Clin. Invest. 1999, 104(7), 895-901). Expression of ERR-α in bone is regulated by estrogen (Bonnelye, E. et al. Mol. Endocrin. 1997, 11, 905-916; Bonnelye, E. et al. J. Cell Biol. 2001, 153, 971-984). ERR-α is maintained throughout osteoblast differentiation stages. Over-expression of ERR-α in rat calvaria osteoblasts, an accepted model of bone differentiation, results in an increase of bone nodule formation, while treatment of rat calvaria osteoblasts with ERR-α antisense results in a decrease of bone nodule formation. ERR-α also regulates osteopontin, a protein believed to be involved in bone matrix formation. Therefore compounds that will modulate ERR-α by increasing its activity can have an anabolic effect for the regeneration of bone density and provide a benefit over current approaches that prevent bone loss, but have no anabolic effect. Such compounds can enhance the activity of the receptor by two possible mechanisms: i) enhancing the association of the receptor with proteins that enhance its activity or improve the stability of the receptor; and ii) increasing the intracellular concentrations of the receptor and consequently increasing its activity. Conversely, with respect to bone diseases that are a result of abnormal bone growth, compounds that will interact with ERR-α and decrease its biological activity may provide a benefit for the treatment of these diseases by retarding bone growth. Antagonism of the association of the receptor with co-activator proteins decreases the activity of the receptor.

ERR-α is also present in cardiac, adipose, and muscle tissue and forms a transcriptional active complex with the PGC-1 co-activator family, co-activators implicated with energy homeostasis, mitochondria biogenesis, hepatic gluconeogenesis and in the regulation of genes involved in fatty acid beta-oxidation (Kamei, Y. et al. Proc. Natl. Acad. Sci. USA 2003, 100(21), 12378-12383). ERR-α regulates the expression of the medium chain acyl-CoA dehydrogenase promoter (MCAD). Medium chain acyl-CoA dehydrogenase is a gene involved in the initial reaction in fatty acid beta-oxidation. It is believed that in the adipose tissue ERR-a regulates energy expenditure through the regulation of MCAD (Sladek, R. et al. Mol. Cell. Biol. 1997, 17, 5400-5409; Vega, R. B. and D. P. Kelly. J. Biol. Chem. 1997, 272, 31693-31699). In antisense experiments in rat calvaria osteoblasts, in addition to the inhibition of bone nodule formation, there was an increase in adipocyte differentiation markers including aP2 and PPAR-γ (Bonnelye, E. et al. Endocrinology 2002, 143, 3658-3670). Recently an ERR-α knockout model has been described that exhibited reduced fat mass relative to the wild type and DNA chip analysis data indicated alteration of the expression levels of genes involved in adipogenesis and energy metabolism (Luo, J. et al. Mol. Cell. Biol. 2003, 23(22), 7947-7956). More recently it has been shown that ERR-α regulates the expression of endothelial nitric oxide synthase, a gene that has a protective mechanism against arteriosclerosis (Sumi, D. and L. J. Ignarro. Proc Natl. Acad. Sci. 2003, 100, 14451-14456). The biochemical evidence supports the involvement of ERR-α in metabolic homeostasis and differentiation of cells into adipocytes. Therefore, compounds interacting with ERR-α can affect energy homeostasis and may therefore provide a benefit for the treatment of obesity and metabolic syndrome related disease indications, including arteriosclerosis and diabetes (Grundy, S. M. et al. Circulation 2004, 109(3), 433-438).

Lion Bioscience AG has disclosed the use of certain pyrazole derivatives as antagonists of ERR-α for treating cancer, osteoporosis, obesity, lipid disorders and cardiovascular disorders and for regulating fertility (European Published Patent Application 1398029).

There is a continuing need for new ERR-α inverse agonists. There is also a need for ERR-α inverse agonists useful for the treatment of conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

SUMMARY OF THE INVENTION

In its many embodiments, the present invention provides novel compounds useful as, for example, ERR-α inverse agonists, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with ERR-α using such compounds or pharmaceutical compositions.

One aspect of the present invention features a compound of Formula (I)

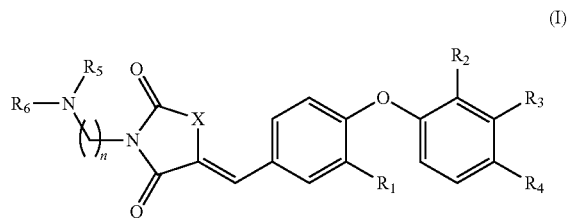

wherein
X is S or O;
n is 1-4
$R_1$ is halo, optionally substituted $C_{1-4}$alkyl, optionally substituted $C_{1-4}$alkoxy, or hydroxyl;
$R_2$ is selected from halo substituted $C_{1-3}$alkyl, cyano, halo, —C(O)NH$_2$, and —C(O)O—C$_{1-4}$alkyl, or alternatively $R_2$ is linked together to $R_3$ to form an aryl fused to the phenyl ring to which $R_2$ and $R_3$ are shown attached;

$R_3$ is H, or alternatively $R_3$ is linked together to $R_2$ to form an aryl ring fused to the phenyl ring to which $R_3$ and $R_2$ are shown attached;

$R_4$ is halo, cyano, halo substituted $C_{1-3}$alkyl, —C≡CH, —C(O)O—$C_{1-4}$alkyl, —C(O)NH$_2$, or —S(O$_2$)—$C_{1-4}$alkyl; and $R_5$ and $R_6$ are independently H or optionally substituted $C_{1-4}$alkyl, or alternatively $R_5$ and $R_6$ are linked together with the N atom to which they are attached to form an optionally substituted 5-9 membered N-containing heteroaryl or optionally substituted 5-7 membered N-containing heterocyclyl;

or an optical isomer, enantiomer, diastereomer, cis-trans isomer, racemate, prodrug or pharmaceutically acceptable salt thereof.

Another aspect of the present invention features a pharmaceutical composition comprising at least one compound of Formula (I) and at least one pharmaceutically acceptable carrier.

The present invention also features a method of treating a subject suffering from or diagnosed with a disease, disorder, or condition mediated by ERR-α activity, comprising administering to the subject a therapeutically effective amount of at least one compound of Formula (I). Such disease, disorder, or condition can include, but is not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance. The therapeutically effective amount of the compound of Formula (I) can be from about 0.1 mg/day to about 5000 mg/day.

The present invention further features a process for making a pharmaceutical composition comprising admixing any of the compounds according to Formula (I) and a pharmaceutically acceptable carrier.

Additional embodiments and advantages of the invention will become apparent from the detailed discussion, schemes, examples, and claims below.

DETAILED DESCRIPTION OF THE INVENTION

This invention relates to novel ERR-α modulators and compositions thereof for the treatment, amelioration, prevention or inhibition of numerous conditions, including but not limited to cancer, arthritis, inflammatory airway disease, bone-related diseases, metabolic disorders, and associated symptoms or complications thereof.

One aspect of the present invention features a compound of Formula (I)

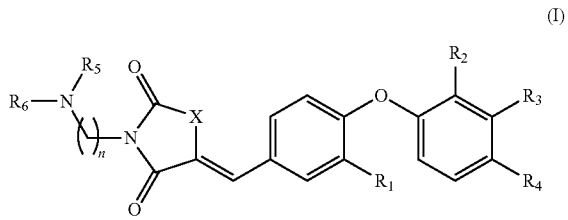

wherein
X is S or O;
n is 1-4
$R_1$ is halo, optionally substituted $C_{1-4}$alkyl, optionally substituted $C_{1-4}$alkoxy, or hydroxyl;
$R_2$ is selected from halo substituted $C_{1-3}$alkyl, cyano, halo, —C(O)NH$_2$, and —C(O)O—$C_{1-4}$alkyl, or alternatively $R_2$ is linked together to $R_3$ to form an aryl fused to the phenyl ring to which $R_2$ and $R_3$ are shown attached;
$R_3$ is H, or alternatively $R_3$ is linked together to $R_2$ to form an aryl ring fused to the phenyl ring to which $R_3$ and $R_2$ are shown attached;
$R_4$ is halo, cyano, halo substituted $C_{1-3}$alkyl, —C≡CH, —C(O)O—$C_{1-4}$alkyl, —C(O)NH$_2$, or —S(O$_2$)—$C_{1-4}$alkyl; and
$R_5$ and $R_6$ are independently H or optionally substituted $C_{1-4}$alkyl, or alternatively $R_5$ and $R_6$ are linked together with the N atom to which they are attached to form an optionally substituted 5-9 membered N-containing heteroaryl or optionally substituted 5-7 membered N-containing heterocyclyl;
or an optical isomer, enantiomer, diastereomer, cis-trans isomer, racemate, prodrug or pharmaceutically acceptable salt thereof.

In particular, the present invention includes a cis-trans isomer of the compound of Formula (I), which has the following structure, wherein X, n, $R_1$, $R_2$, $R_3$, $R_4$, $R_5$, and $R_6$ are as described above:

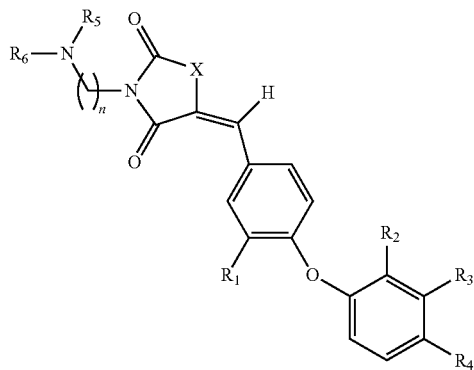

Particularly, $R_1$ is unsubstituted $C_{1-4}$alkoxy. More particularly, $R_1$ is —O—CH$_3$.
Particularly, $R_2$ is CF$_3$.
Particularly, $R_3$ is H.
Particularly, $R_2$ is linked together to $R_3$ to form an aryl fused to the phenyl ring to which $R_2$ and $R_3$ are shown attached. More particularly, $R_2$ is linked together to $R_3$ to form a phenyl fused to the phenyl ring to which $R_2$ and $R_3$ are shown attached.

Particularly, $R_2$ is $CF_3$ and $R_3$ is H.

Particularly, $R_4$ is cyano. More particularly, $R_4$ is cyano and $R_2$ is $CF_3$.

Particularly, X is S.

Particularly, the present invention includes a compound of Formula (I) wherein
$R_1$ is —O—$CH_3$;
$R_2$ is $CF_3$;
$R_3$ is H;
$R_4$ is CN;
X is S;
$R_5$ and $R_6$ are independently $C_{1-4}$alkyl, or alternatively $R_5$ and $R_6$ are linked together with the N atom to which they are attached to form an optionally substituted member selected from or an optical isomer, enantiomer, diastereomer, racemate, cis-trans isomer, prodrug or pharmaceutically acceptable salt thereof.

More particularly, an example of the present invention includes compounds of Formula (I) wherein $R_5$ and $R_6$ are —$CH_3$, or alternatively $R_5$ and $R_6$ are linked together with the N atom to which they are attached to form an optionally substituted member selected from It is an embodiment of the present invention to provide a compound selected from:
4-{2-Methoxy-4-[3-(2-morpholin-4-yl-ethyl)-2,4-dioxo-thiazolidin-5-ylidenemethyl]-phenoxy}-3-trifluoromethyl-benzonitrile;
4-{4-[3-(2-Dimethylamino-ethyl)-2,4-dioxo-thiazolidin-5-ylidenemethyl]-2-methoxy-phenoxy}-3-trifluoromethyl-benzonitrile;
4-{4-[2,4-Dioxo-3-(2-pyrrolidin-1-yl-ethyl)-thiazolidin-5-ylidenemethyl]-2-methoxy-phenoxy}-3-trifluoromethyl-benzonitrile;
4-(2-Methoxy-4-{3-[2-(4-methyl-piperazin-1-yl)-ethyl]-2,4-dioxo-thiazolidin-5-ylidenemethyl}-phenoxy)-3-trifluoromethyl-benzonitrile;
4-{4-[3-(2-Dimethylamino-ethyl)-2,4-dioxo-thiazolidin-5-ylidenemethyl]-2-fluoro-phenoxy}-3-trifluoromethyl-benzonitrile;
4-{2-Fluoro-4-[3-(2-morpholin-4-yl-ethyl)-2,4-dioxo-thiazolidin-5-ylidenemethyl]-phenoxy}-3-trifluoromethyl-benzonitrile;
4-{4-[3-(2-Diethylamino-ethyl)-2,4-dioxo-thiazolidin-5-ylidenemethyl]-2-methoxy-phenoxy}-3-trifluoromethyl-benzonitrile;
4-{4-[3-(2-Imidazol-1-yl-ethyl)-2,4-dioxo-thiazolidin-5-ylidenemethyl]-2-methoxy-phenoxy}-3-trifluoromethyl-benzonitrile;
4-{4-[2,4-Dioxo-3-(2-piperidin-1-yl-ethyl)-thiazolidin-5-ylidenemethyl]-2-methoxy-phenoxy}-3-trifluoromethyl-benzonitrile;
4-{4-[2,4-Dioxo-3-(2-pyrazol-1-yl-ethyl)-thiazolidin-5-ylidenemethyl]-2-methoxy-phenoxy}-3-trifluoromethyl-benzonitrile;
4-{4-[2,4-Dioxo-3-(2-[1,2,4]triazol-1-yl-ethyl)-thiazolidin-5-ylidenemethyl]-2-methoxy-phenoxy}-3-trifluoromethyl-benzonitrile;
4-{4-[3-(2-Azepan-1-yl-ethyl)-2,4-dioxo-thiazolidin-5-ylidenemethyl]-2-methoxy-phenoxy}-3-trifluoromethyl-benzonitrile;
4-{4-[2,4-Dioxo-3-(2-pyrrol-1-yl-ethyl)-thiazolidin-5-ylidenemethyl]-2-methoxy-phenoxy}-3-trifluoromethyl-benzonitrile; and
4-{4-[2,4-Dioxo-3-(2-pyrrolidin-1-yl-ethyl)-thiazolidin-5-ylidenemethyl]-2-fluoro-phenoxy}-3-trifluoromethyl-benzonitrile.

More particularly, the compound is

More particularly, the compound is

More particularly, the compound is

More particularly, the compound is

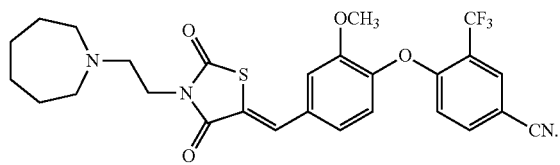 [SMILES: COc1cc(/C=C2\SC(=O)N(CCN3CCCCCC3)C2=O)ccc1Oc1ccc(C#N)cc1C(F)(F)F]

Another aspect of the present invention features a pharmaceutical composition comprising at least one compound of Formula (I) and at least one pharmaceutically acceptable carrier. Particularly, a pharmaceutical composition of the present invention can further comprise at least one additional agent, drug, medicament, antibody and/or inhibitor for treating, ameliorating or preventing an ERR-α mediated disease. More particularly, a pharmaceutical composition of the present invention comprises a compound selected from:

4-{2-Methoxy-4-[3-(2-morpholin-4-yl-ethyl)-2,4-dioxo-thiazolidin-5-ylidenemethyl]-phenoxy}-3-trifluoromethyl-benzonitrile;

4-{4-[3-(2-Dimethylamino-ethyl)-2,4-dioxo-thiazolidin-5-ylidenemethyl]-2-methoxy-phenoxy}-3-trifluoromethyl-benzonitrile;

4-{4-[2,4-Dioxo-3-(2-pyrrolidin-1-yl-ethyl)-thiazolidin-5-ylidenemethyl]-2-methoxy-phenoxy}-3-trifluoromethyl-benzonitrile; and 4-(2-Methoxy-4-{3-[2-(4-methyl-piperazin-1-yl)-ethyl]-2,4-dioxo-thiazolidin-5-ylidenemethyl}-phenoxy)-3-trifluoromethyl-benzonitrile;

4-{4-[3-(2-Dimethylamino-ethyl)-2,4-dioxo-thiazolidin-5-ylidenemethyl]-2-fluoro-phenoxy}-3-trifluoromethyl-benzonitrile;

4-{2-Fluoro-4-[3-(2-morpholin-4-yl-ethyl)-2,4-dioxo-thiazolidin-5-ylidenemethyl]-phenoxy}-3-trifluoromethyl-benzonitrile;

4-{4-[3-(2-Diethylamino-ethyl)-2,4-dioxo-thiazolidin-5-ylidenemethyl]-2-methoxy-phenoxy}-3-trifluoromethyl-benzonitrile;

4-{4-[3-(2-Imidazol-1-yl-ethyl)-2,4-dioxo-thiazolidin-5-ylidenemethyl]-2-methoxy-phenoxy}-3-trifluoromethyl-benzonitrile;

4-{4-[2,4-Dioxo-3-(2-piperidin-1-yl-ethyl)-thiazolidin-5-ylidenemethyl]-2-methoxy-phenoxy}-3-trifluoromethyl-benzonitrile;

4-{4-[2,4-Dioxo-3-(2-pyrazol-1-yl-ethyl)-thiazolidin-5-ylidenemethyl]-2-methoxy-phenoxy}-3-trifluoromethyl-benzonitrile;

4-{4-[2,4-Dioxo-3-(2-[1,2,4]triazol-1-yl-ethyl)-thiazolidin-5-ylidenemethyl]-2-methoxy-phenoxy}-3-trifluoromethyl-benzonitrile;

4-{4-[3-(2-Azepan-1-yl-ethyl)-2,4-dioxo-thiazolidin-5-ylidenemethyl]-2-methoxy-phenoxy}-3-trifluoromethyl-benzonitrile;

4-{4-[2,4-Dioxo-3-(2-pyrrol-1-yl-ethyl)-thiazolidin-5-ylidenemethyl]-2-methoxy-phenoxy}-3-trifluoromethyl-benzonitrile; and 4-{4-[2,4-Dioxo-3-(2-pyrrolidin-1-yl-ethyl)-thiazolidin-5-ylidenemethyl]-2-fluoro-phenoxy}-3-trifluoromethyl-benzonitrile.

More particularly, a pharmaceutical composition of the present invention comprises at least

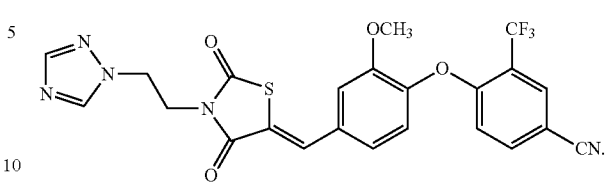

The present invention also features a method of treating a subject suffering from or diagnosed with a disease, disorder, or condition mediated by ERR-α activity, comprising administering to the subject a therapeutically effective amount of at least one compound of Formula (I).

The present invention also features a method for preventing or inhibiting the progression of an ERR-α-mediated condition in a subject in need thereof, comprising administering to said subject a therapeutically effective amount of at least one compound of Formula (I).

The present invention also features a method for treating a prediabetic condition in a subject in need thereof, comprising administering to said subject a therapeutically effective amount of at least one compound of Formula (I).

Such disease, disorder, or condition can include, but is not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

According to one aspect of the invention, the disclosed compounds and compositions are useful for the amelioration of symptoms associated with, the treatment of, and the prevention or inhibiting the progression of, the following conditions and diseases: bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, and repetitive stress injury.

According to another aspect of the invention, the disclosed compounds and compositions are useful for the amelioration of symptoms associated with, the treatment of, and preventing and/or inhibiting the progression of, the following conditions and diseases: periodontal disease, chronic inflammatory airway disease, chronic bronchitis, and chronic obstructive pulmonary disease.

According to a further aspect of the invention, the disclosed compounds and compositions are useful for the amelioration of symptoms associated with, the treatment of, and preventing and/or inhibiting the progression of breast cancer.

According to yet another aspect of the invention, the disclosed compounds and compositions are useful for the amelioration of symptoms associated with, the treatment of, and preventing and/or inhibiting the progression of, the following conditions and diseases: metabolic syndrome, obesity, disorders of energy homeostasis, diabetes, lipid disorders, cardiovascular disorders, artherosclerosis, hyperglycemia, elevated blood glucose level, and insulin resistance.

Particularly, a method of the present invention comprises administering to the subject a therapeutically effective amount of (a) at least one compound of Formula (I); and (b) at least one additional agent selected from a second ERR-α inverse agonist, an ERR-α antagonist, a glucokinase modulator, an anti-diabetic agent, an anti-obesity agent, a lipid lowering agent, an anti-thrombotic agent, direct thrombin inhibitor, and a blood pressure lowering agent, said administration being in any order. More particularly, the additional agent in (b) is a second ERR-α inverse agonist different from the compound in (a). More particularly, the additional agent in (b) is an anti-obesity agent selected from CB1 antagonists, monoamine reuptake inhibotors, and lipase inhibitors. More particularly, the additional agent in (b) is selected from rimonabant, sibutramine, and orlistat.

The present invention also features a method for treating or inhibiting the progression of one or more ERR-α-mediated conditions, said method comprising administering to a patient in need of treatment a pharmaceutically effective amount of a composition of the invention.

It is a further embodiment of the invention to provide a process for making a pharmaceutical composition comprising admixing any of the compounds according to Formula (I) and a pharmaceutically acceptable carrier.

The invention also features pharmaceutical compositions which include, without limitation, one or more of the disclosed compounds, and pharmaceutically acceptable carriers or excipients.

In a further embodiment of the invention, a method for treating or ameliorating an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In a further embodiment of the invention, a method for preventing or inhibiting the progression of an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In yet another embodiment of the invention, a method for treating a prediabetic condition in a subject in need thereof, comprises administering to said subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

Unless otherwise noted, "alkyl" as used herein, whether used alone or as part of a substituent group, refers to a saturated, branched, or straight-chain monovalent hydrocarbon radical derived by the removal of one hydrogen atom from a single carbon atom of a parent alkane. Typical alkyl groups include, but are not limited to, methyl; ethyls such as ethanyl; propyls such as propan-1-yl, propan-2-yl, cyclopropan-1-yl; butyls such as butan-1-yl, butan-2-yl, 2-methyl-propan-1-yl, 2-methyl-propan-2-yl, cyclobutan-1-yl and the like. In preferred embodiments, the alkyl groups are $C_{1-6}$alkyl, with $C_{1-3}$ being particularly preferred. "Alkoxy" radicals are oxygen ethers formed from the previously described straight or branched chain alkyl groups. In some embodiments, the alkyl or alkoxy are independently substituted with one to five, preferably one to three groups including, but not limited to, oxo, amino, alkoxy, carboxy, heterocyclyl, hydroxyl, and halo (F, Cl, Br, or I).

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl is substituted with one to five, preferably one to three groups including, but not limited to, oxo, amino, alkoxy, carboxy, heterocyclyl, hydroxyl, and halo.

The term "alkynyl" refers to an unsaturated branched, straight-chain or cyclic monovalent hydrocarbon radical, which has at least one carbon-carbon triple bond, derived by the removal of one hydrogen atom from a single carbon atom of a parent alkyne. Typical alkynyl groups include, but are not limited to, ethynyl; propynyls such as prop-1-yn-1-yl, prop- 2-yn-1-yl, etc.; butynyls such as but-1-yn-1-yl, but-1-yn-3-yl, but-3-yn-1-yl, etc.; and the like. In some embodiments, the alkynyl is substituted with one to five, preferably one to three groups including, but not limited to, oxo, amino, alkoxy, carboxy, heterocyclyl, hydroxyl, and halo.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic. Heteroaromatic rings may contain 1-4 heteroatoms selected from O, N, and S. Examples include but are not limited to, radicals derived from carbazole, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, "heteroaryl" is substituted. For instance, "heteroaryl" can be substituted with, e.g., optionally substituted $C_{1-6}$alkyl, $C_{2-6}$alkenyl, $C_{2-6}$alkynyl, halo, hydroxyl, —CN, —C(O)OH, —C(O)O—$C_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl. In some embodiments, "aryl" is substituted. For instance, "aryl" can be substituted with, e.g., optionally substituted $C_{1-6}$alkyl, $C_{2-6}$alkenyl, $C_{2-6}$alkynyl, halo, hydroxyl, —CN, —C(O)OH, —C(O)O—$C_{1-4}$alkyl, —C(O)NR'R", —SR', —OR', —C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "heterocyclyl" or "heterocycle" is a 3- to 8-member saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone. In some embodiments, "heterocyclyl" or "heterocycle" are independently substituted. For instance, "heterocyclyl" or "heterocycle" can be substituted with, e.g., optionally substituted $C_{1-6}$alkyl, $C_{2-6}$alkenyl, $C_{2-6}$alkynyl, halo, hydroxyl, —CN, —C(O)OH, —C(O)O—$C_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "oxo" whether used alone or as part of a substituent group refers to an O═ to either a carbon or a sulfur atom. For example, phthalimide and saccharin are examples of compounds with oxo substituents.

The term "cis-trans isomer" refers to stereoisomeric olefins or cycloalkanes (or hetero-analogues) which differ in the positions of atoms (or groups) relative to a reference plane: in the cis-isomer the atoms are on the same side; in the trans-isomer they are on opposite sides.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "inverse agonist" as used herein refers to compounds or substances that have the ability to decrease the constitutive level of receptor activation in the absence of an agonist instead of only blocking the activation induced by agonist binding at the receptor.

Metabolic disorders, diseases, or conditions include, but are not limited to, diabetes, obesity, and associated symptoms or complications thereof. They include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (or Metabolic Syndrome), hyperglycemia, elevated blood glucose level, and insulin resistance. A condition such as IGT or IFG is also known as a "prediabetic condition" or "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

B) Compounds

Representative compounds of the present invention are listed in Table I below:

TABLE I

| STRUCTURE | COMPOUND # | NAME |
|---|---|---|
| 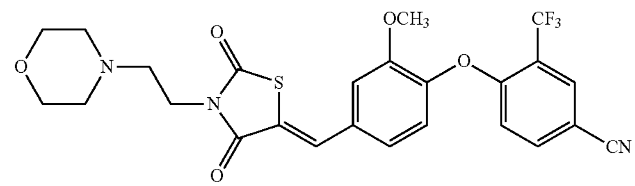 [SMILES: COc1cc(/C=C2\SC(=O)N(CCN3CCOCC3)C2=O)ccc1Oc1ccc(C#N)cc1C(F)(F)F] | 1 | 4-{2-Methoxy-4-[3-(2-morpholin-4-yl-ethyl)-2,4-dioxo-thiazolidin-5-ylidenemethyl]-phenoxy}-3-trifluoromethyl-benzonitrile |
| 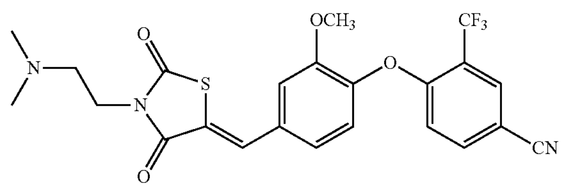 [SMILES: COc1cc(/C=C2\SC(=O)N(CCN(C)C)C2=O)ccc1Oc1ccc(C#N)cc1C(F)(F)F] | 2 | 4-{4-[3-(2-Dimethylamino-ethyl)-2,4-dioxo-thiazolidin-5-ylidenemethyl]-2-methoxy-phenoxy}-3-trifluoromethyl-benzonitrile |
| 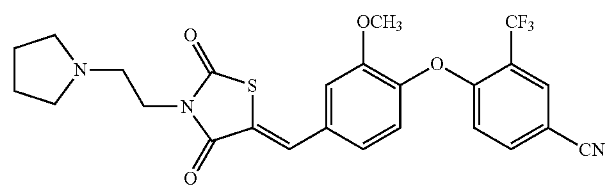 [SMILES: COc1cc(/C=C2\SC(=O)N(CCN3CCCC3)C2=O)ccc1Oc1ccc(C#N)cc1C(F)(F)F] | 3 | 4-{4-[2,4-Dioxo-3-(2-pyrrolidin-1-yl-ethyl)-thiazolidin-5-ylidenemethyl]-2-methoxy-phenoxy}-3-trifluoromethyl-benzonitrile |
| 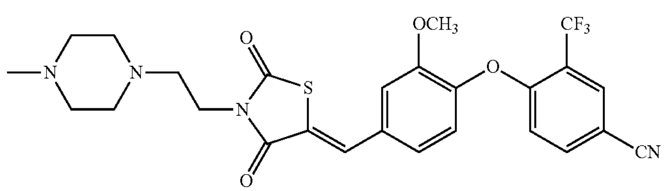 [SMILES: COc1cc(/C=C2\SC(=O)N(CCN3CCN(C)CC3)C2=O)ccc1Oc1ccc(C#N)cc1C(F)(F)F] | 4 | 4-(2-Methoxy-4-{3-[2-(4-methyl-piperazin-1-yl)-ethyl]-2,4-dioxo-thiazolidin-5-ylidenemethyl}-phenoxy)-3-trifluoromethyl-benzonitrile |
| 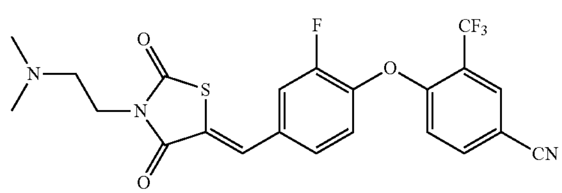 [SMILES: CN(C)CCN1C(=O)S/C(=C\c2ccc(Oc3ccc(C#N)cc3C(F)(F)F)c(F)c2)C1=O] | 5 | 4-{4-[3-(2-Dimethylamino-ethyl)-2,4-dioxo-thiazolidin-5-ylidenemethyl]-2-fluoro-phenoxy}-3-trifluoromethyl-benzonitrile |
| 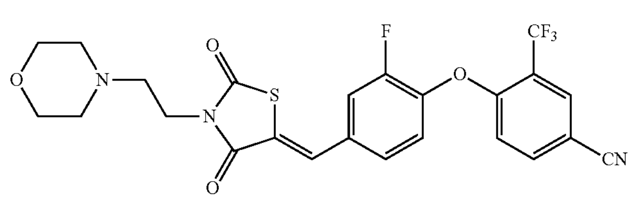 [SMILES: N#Cc1ccc(Oc2ccc(/C=C3\SC(=O)N(CCN4CCOCC4)C3=O)cc2F)c(C(F)(F)F)c1] | 6 | 4-{2-Fluoro-4-[3-(2-morpholin-4-yl-ethyl)-2,4-dioxo-thiazolidin-5-ylidenemethyl]-phenoxy}-3-trifluoromethyl-benzonitrile |

TABLE I-continued

| STRUCTURE | COMPOUND # | NAME |
|---|---|---|
| 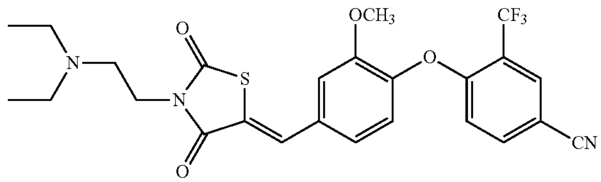 [SMILES: CCN(CC)CCN1C(=O)S/C(=C\c2ccc(Oc3ccc(C#N)cc3C(F)(F)F)c(OC)c2)C1=O] | 7 | 4-{4-[3-(2-Diethylamino-ethyl)-2,4-dioxo-thiazolidin-5-ylidenemethyl]-2-methoxy-phenoxy}-3-trifluoromethyl-benzonitrile |
| 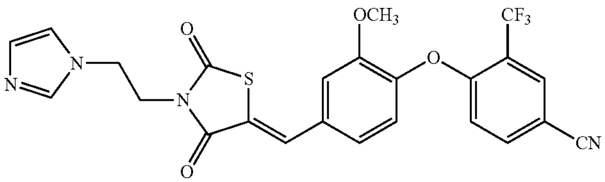 [SMILES: COc1cc(/C=C2\SC(=O)N(CCn3ccnc3)C2=O)ccc1Oc1ccc(C#N)cc1C(F)(F)F] | 8 | 4-{4-[3-(2-Imidazol-1-yl-ethyl)-2,4-dioxo-thiazolidin-5-ylidenemethyl]-2-methoxy-phenoxy}-3-trifluoromethyl-benzonitrile |
| 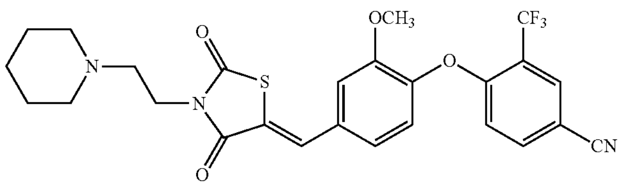 [SMILES: COc1cc(/C=C2\SC(=O)N(CCN3CCCCC3)C2=O)ccc1Oc1ccc(C#N)cc1C(F)(F)F] | 9 | 4-{4-[2,4-Dioxo-3-(2-piperidin-1-yl-ethyl)-thiazolidin-5-ylidenemethyl]-2-methoxy-phenoxy}-3-trifluoromethyl-benzonitrile |
| 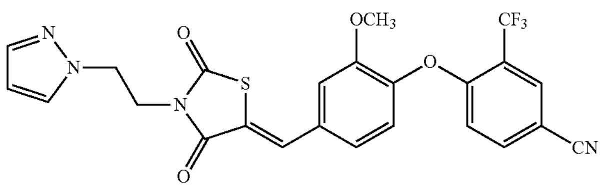 [SMILES: COc1cc(/C=C2\SC(=O)N(CCn3cccn3)C2=O)ccc1Oc1ccc(C#N)cc1C(F)(F)F] | 10 | 4-{4-[2,4-Dioxo-3-(2-pyrazol-1-yl-ethyl)-thiazolidin-5-ylidenemethyl]-2-methoxy-phenoxy}-3-trifluoromethyl-benzonitrile |
| 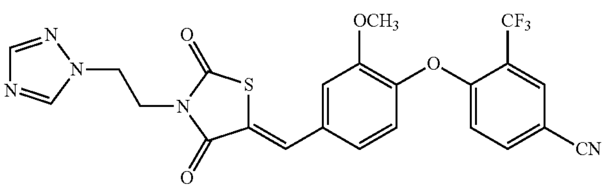 | 11 | 4-{4-[2,4-Dioxo-3-(2-[1,2,4]triazol-1-yl-ethyl)-thiazolidin-5-ylidenemethyl]-2-methoxy-phenoxy}-3-trifluoromethyl-benzonitrile |
| 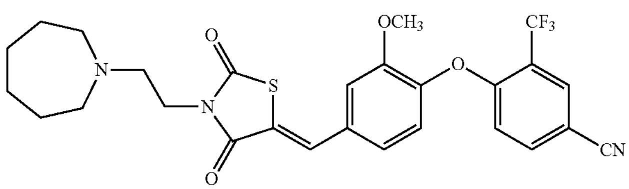 [SMILES: COc1cc(/C=C2\SC(=O)N(CCN3CCCCCC3)C2=O)ccc1Oc1ccc(C#N)cc1C(F)(F)F] | 12 | 4-{4-[3-(2-Azepan-1-yl-ethyl)-2,4-dioxo-thiazolidin-5-ylidenemethyl]-2-methoxy-phenoxy}-3-trifluoromethyl-benzonitrile |
| 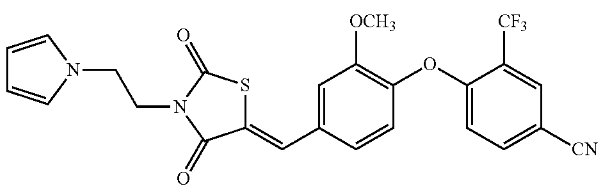 | 13 | 4-{4-[2,4-Dioxo-3-(2-pyrrol-1-yl-ethyl)-thiazolidin-5-ylidenemethyl]-2-methoxy-phenoxy}-3-trifluoromethyl-benzonitrile |
| 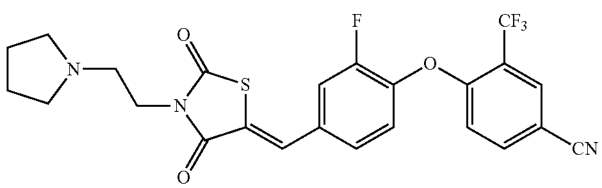 [SMILES: N#Cc1ccc(Oc2ccc(/C=C3\SC(=O)N(CCN4CCCC4)C3=O)cc2F)c(C(F)(F)F)c1] | 14 | 4-{4-[2,4-Dioxo-3-(2-pyrrolidin-1-yl-ethyl)-thiazolidin-5-ylidenemethyl]-2-fluoro-phenoxy}-3-trifluoromethyl-benzonitrile |

C) Synthesis

The invention provides methods of making the disclosed compounds according to traditional organic synthetic methods as well as matrix or combinatorial synthetic methods. Scheme 1 describes suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Scheme 1 and Examples 1 through 4. Compounds analogous to the target compounds of these examples can be made according to similar routes. The disclosed compounds are useful as pharmaceutical agents as described herein.

Abbreviations or acronyms useful herein include:
AIBN (2,2'-Azobisisobutyronitrile)
Boc (tert butyl carbamate)
BOP (Benzotriazol-1-yloxy)tris(dimethylamino)phosphonium hexfluorophosphate)
BuLi (butyllithium)
DIBAL-H (Diisobutylaluminum hydride)
DMAP (4-(dimethylamino)pyridine)
DME (Ethylene glycol dimethyl ether)
DMF (dimethylformamide)
DMPU (1,3-Dimethyl-3,4,5,6-tetrahydro-2(1H)-pyrimidinone)
DMSO (methyl sulfoxide)
EDC (N-(3-Dimethylaminopropyl)-N'-ethylcarbodiimide)
EDCI (1-(3-Dimethylaminopropyl)-3-ethylcarbodiimide hydrochloride)
Et (ethyl)
EtOAc (ethyl acetate)
h or hr (hour(s))
HATU (O-(7-Azabenzotriazol-1-yl)-N,N,N',N'-tetramethyluronium hexafluorophosphate)
HMPA (Hexamethylphosphoramide)
HOBt (1-Hydroxybenzotriazole monohydrate)
LCMS (high pressure liquid chromatography with mass spectrometer)
LDA (Lithium diisopropylamide)
LHMDS (lithium hexamethyl disilazide)
Me (methyl)
Mg (milligram)
MOM (Methoxymethyl)
NaHMDS (sodium hexamethyl disilazide)
NaO$^t$Bu (sodium tert-butoxide)
NBS (N-Bromosuccinimide)
NMP (N-Methyl Pyrrolidinone)
rt or RT (room temperature)
SPE (solid phase extraction)
TBTU (O-Benzotriazol-1-yl-N,N,N',N'-tetramethyluronium hexafluorophosphate)
TEMPO (2,2,6,6-tetramethyl-1-piperdinyloxy, free radical)
TFA (trifluoroacetic acid);
THF (tetrahydrofuran)
TLC (thin layer chromatography)

GENERAL GUIDANCE

Scheme 1

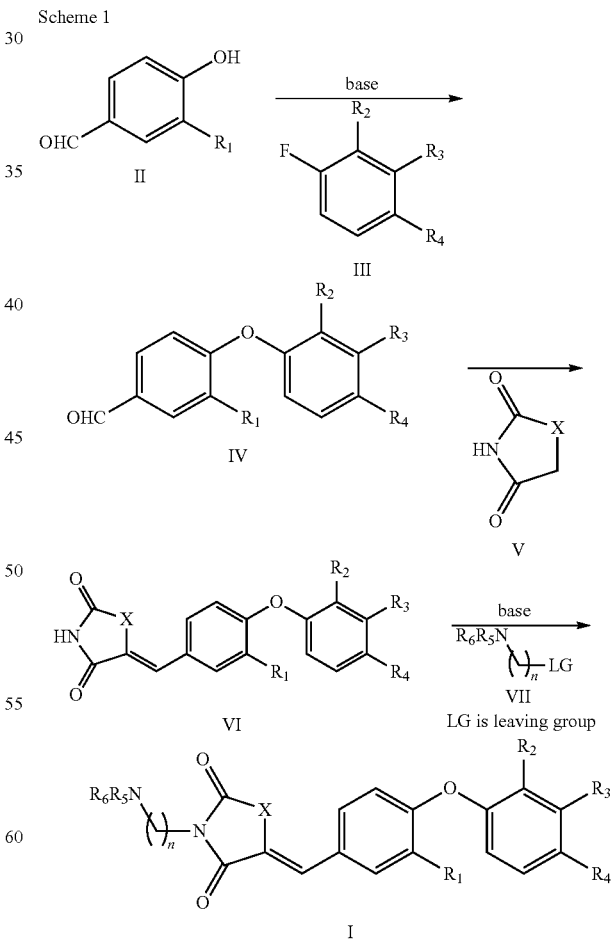

The compounds of Formula I, wherein n, X, $R_1$, $R_2$, $R_3$, $R_4$, $R_5$ and $R_6$ are defined herein, can be synthesized as outlined by the general synthetic route illustrated in Scheme 1. Treatment of an appropriate hydoxybenzaldehyde II and aryl fluoride III, both of which are either commercially available or can be made from commercially available starting materials, with a base such as $K_2CO_3$ in a solvent such as DMF at a temperature preferably between 25-150° C. can provide the phenoxyaldehyde IV. Knoevenagel reaction of aldehyde IV with the cyclic dione V in the presence of a catalytic amount of base such as piperidine and an acid such as benzoic acid can provide the phenoxy cyclic dione VI. The Knoevenagel reaction is typically performed in an aprotic solvent such as toluene at a temperature preferably between 100-200° C. The reaction between aldehyde IV and cyclic dione V may also be performed with a base such as sodium acetate in a solvent such as acetonitrile at a temperature preferably between 50-150° C. or in the presence of ammonium acetate in acetic acid at a temperature preferably between 50-150° C. Treatment of dione VI with an appropriate amine VII, wherein LG is a leaving group such as chloride, bromide, iodide or mesylate, in the presence of a base such as $K_2CO_3$ in a solvent such as DMF at a temperature preferably between 25-150° C. can provide the compounds of Formula I.

EXAMPLES

Example 1

4-{2-Methoxy-4-[3-(2-morpholin-4-yl-ethyl)-2,4-dioxo-thiazolidin-5-ylidenemethyl]-phenoxy}-3-trifluoromethyl-benzonitrile

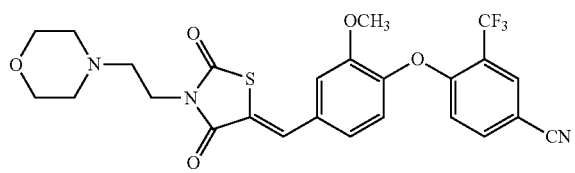 [SMILES: COc1cc(/C=C2\SC(=O)N(CCN3CCOCC3)C2=O)ccc1Oc1ccc(C#N)cc1C(F)(F)F]

A. 4-(4-Formyl-2-methoxy-phenoxy)-3-trifluoromethyl-benzonitrile

A solution of vanillin (1.65 g, 10.86 mmol) and 4-fluoro-3-trifluoromethyl-benzonitrile (10.26 mmol) in DMF (15 mL) was treated with $K_2CO_3$ (2.83 g, 21.72 mmol), and the mixture was heated in an oil bath at 80° C. for 12 h. The reaction was cooled to RT and partitioned between EtOAc and $H_2O$. The organic phase was washed with water (3×), dried over $Na_2SO_4$ and concentrated in vacuo. Silica gel chromatography (EtOAc/hexanes) afforded the title compound. $^1$H NMR (400 Hz, CDCl$_3$) δ 10.00 (s, 1H), 8.00 (m, 1H), 7.68 (dd, 1H), 7.58-7.53 (m, 2H), 7.29 (d, 1H), 6.75 (d, 1H), 3.83 (s, 3H); LC/MS (m/z) [M+1]$^+$ 322.1 (calculated for $C_{16}H_{11}F_3NO_3$, 322.06).

B. 4-[4-(2,4-Dioxo-thiazolidin-5-ylidenemethyl)-2-methoxy-phenoxy]-3-trifluoromethyl-benzonitrile Thiazolidine-2,4-dione (2.55 g, 21.79 mmol) and 4-(4-Formyl-2-methoxy-phenoxy)-3-trifluoromethyl-benzonitrile (21.79 mmol) were dissolved in toluene (150 mL) and treated with benzoic acid (3.27 mmol) and piperidine (2.83 mmol). The flask was equipped with a Dean-Stark trap, and the reaction was refluxed in a 130° C. oil bath for 12 h. After cooling to RT, the product was collected by filtration and triturated with hexanes to afford the title compound. $^1$H NMR (400 Hz, DMSO-d6) δ 12.68 (NH), 8.32 (d, 1H), 8.00 (dd, 1H), 7.83 (s, 1H), 7.49 (d, 1H), 7.36 (d, 1H), 7.26 (dd, 1H), 6.90 (d, 1H), 3.77 (s, 3H); LC/MS (m/z) [M+1]$^+$ 421.0 (calculated for $C_{19}H_{12}F_3N_2O_4S$, 421.04).

C. 4-{2-Methoxy-4-[3-(2-morpholin-4-yl-ethyl)-2,4-dioxo-thiazolidin-5-ylidenemethyl]-phenoxy}-3-trifluoromethyl-benzonitrile A solution of 4-[4-(2,4-Dioxo-thiazolidin-5-ylidenemethyl)-2-methoxy-phenoxy]-3-trifluoromethyl-benzonitrile (40 mg, 0.095 mmol) and 4-(2-Chloro-ethyl)-morpholine (0.095 mmol) in DMF (1.5 mL) was treated with $K_2CO_3$ (33 mg, 0.24 mmol) and heated to 80° C. in an aluminum heating block. After 12 h, the reaction was cooled to RT and partitioned between EtOAc (5 mL) and $H_2O$ (5 mL). The organic phase was washed with $H_2O$ (2×5 mL), dried over $Na_2SO_4$ and concentrated in vacuo. Silica gel chromatography (MeOH/$CH_2Cl_2$) afforded the title compound. $^1$H NMR (400 Hz, CDCl$_3$) δ 7.97 (d, 1H), 7.87 (s, 1H), 7.68 (dd, 1H), 7.19 (m, 3H), 6.76 (d, 1H), 3.90 (t, 2H), 3.82 (s, 3H), 3.67 (bs, 4H), 2.64 (t, 2H), 2.51 (bs, 4H); LC/MS (m/z) [M+1]$^+$ 534.2 (calculated for $C_{25}H_{23}F_3N_3O_5S$, 534.12).

Example 2

4-{4-[3-(2-Dimethylamino-ethyl)-2,4-dioxo-thiazolidin-5-ylidenemethyl]-2-methoxy-phenoxy}-3-trifluoromethyl-benzonitrile

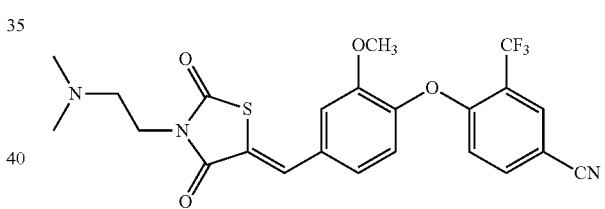

The title compound was prepared essentially as described in Example 1C except that (2-Chloro-ethyl)-dimethyl-amine was used in the place of 4-(2-Chloro-ethyl)-morpholine. $^1$H NMR (400 Hz, CDCl$_3$) δ 7.97 (d, 1H), 7.87 (s, 1H), 7.68 (dd, 1H), 7.19 (m, 3H), 6.78 (d, 1H), 3.90 (t, 2H), 3.81 (s, 3H), 2.61 (bt, 2H), 2.31 (bs, 6H); LC/MS (m/z) [M+1]$^+$ 492.1 (calculated for $C_{23}H_{21}F_3N_3O_4S$, 492.11).

Example 3

4-{4-[2,4-Dioxo-3-(2-pyrrolidin-1-yl-ethyl)-thiazolidin-5-ylidenemethyl]-2-methoxy-phenoxy}-3-trifluoromethyl-benzonitrile

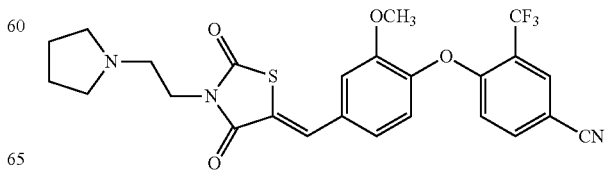

The title compound was prepared essentially as described in Example 1C except that 1-(2-Chloro-ethyl)-pyrrolidine was used in the place of 4-(2-Chloro-ethyl)-morpholine. $^1$H NMR (400 Hz, CDCl$_3$) δ 7.90 (d, 1H), 7.80 (s, 1H), 7.61 (dd, 1H), 7.11 (m, 3H), 6.68 (d, 1H), 3.92 (t, 2H), 3.72 (s, 3H), 2.87 (bs, 2H), 2.72 (bs, 4H), 1.80 (bs, 4H); LC/MS (m/z) [M+1]$^+$ 518.1 (calculated for C$_{25}$H$_{23}$F$_3$N$_3$O$_4$S, 518.13).

Example 4

4-(2-Methoxy-4-{3-[2-(4-methyl-piperazin-1-yl)-ethyl]-2,4-dioxo-thiazolidin-5-ylidenemethyl}-phenoxy)-3-trifluoromethyl-benzonitrile

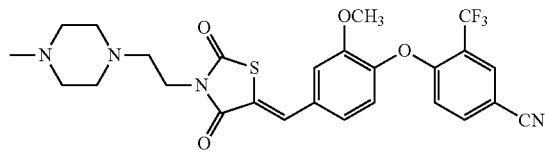 [SMILES: COc1cc(/C=C2\SC(=O)N(CCN3CCN(C)CC3)C2=O)ccc1Oc1ccc(C#N)cc1C(F)(F)F]

The title compound was prepared essentially as described in Example 1C except that 1-(2-Chloro-ethyl)-4-methyl-piperazine was used in the place of 4-(2-Chloro-ethyl)-morpholine. $^1$H NMR (400 Hz, CDCl$_3$) δ 7.88 (d, 1H), 7.69 (s, 1H), 7.59 (dd, 1H), 7.25 (d, 1H), 7.21 (d, 1H), 7.09 (d, 1H), 6.70 (d, 1H), 3.93 (br s, 2H), 3.76-3.67 (m, 5H), 3.42 (br s, 2H), 3.10 (t, 2H), 2.53 (br s, 4H), 2.34 (s, 3H); LC/MS (m/z) [M+1]$^+$ 547.4 (calculated for C$_{26}$H$_{26}$F$_3$N$_4$O$_4$S, 547.15).

Example 5

4-{4-[3-(2-Dimethylamino-ethyl)-2,4-dioxo-thiazolidin-5-ylidenemethyl]-2-fluoro-phenoxy}-3-trifluoromethyl-benzonitrile

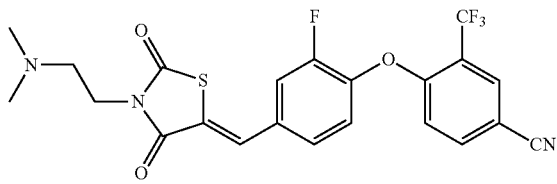 [SMILES: CN(C)CCN1C(=O)S/C(=C\c2ccc(Oc3ccc(C#N)cc3C(F)(F)F)c(F)c2)C1=O]

The title compound was prepared using 4-[4-(2,4-Dioxo-thiazolidin-5-ylidenemethyl)-2-fluoro-phenoxy]-3-trifluoromethyl-benzonitrile and (2-Chloro-ethyl)-dimethyl-amine as described in Example 1. $^1$H NMR (400 Hz, CDCl$_3$) δ 7.95 (s, 1H), 7.76 (s, 1H), 7.69 (dd, 1H), 7.27 (m, 3H), 6.84 (d, 1H), 3.91 (t, 2H), 2.76 (bt, 2H), 2.40 (s, 6H); LC/MS (m/z) [M+1]$^+$ 480.1 (calculated for C$_{22}$H$_{18}$F$_4$N$_3$O$_3$S, 480.45).

Example 6

4-{2-Fluoro-4-[3-(2-morpholin-4-yl-ethyl)-2,4-dioxo-thiazolidin-5-ylidenemethyl]-phenoxy}-3-trifluoromethyl-benzonitrile

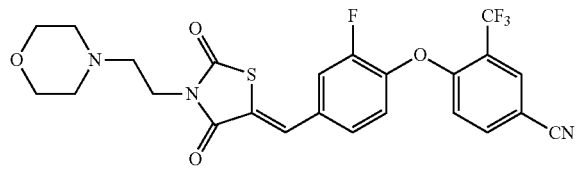 [SMILES: N#Cc1ccc(Oc2ccc(/C=C3\SC(=O)N(CCN4CCOCC4)C3=O)cc2F)c(C(F)(F)F)c1]

The title compound was prepared using 4-[4-(2,4-Dioxo-thiazolidin-5-ylidenemethyl)-2-fluoro-phenoxy]-3-trifluoromethyl-benzonitrile and 4-(2-Chloro-ethyl)-morpholine as described in Example 1. $^1$H NMR (400 Hz, CDCl$_3$) δ 8.01 (s, 1H), 7.83 (s, 1H), 7.74 (dd, 1H), 7.34 (m, 3H), 6.91 (d, 1H), 3.92 (t, 2H), 3.69 (bt, 2H), 2.69 (bt, 2H), 2.57 (bs, 2H); LC/MS (m/z) [M+1]$^+$ 522.2 (calculated for C$_{24}$H$_{20}$F$_4$N$_3$O$_4$S, 522.49).

Example 7

4-{4-[3-(2-Diethylamino-ethyl)-2,4-dioxo-thiazolidin-5-ylidenemethyl]-2-methoxy-phenoxy}-3-trifluoromethyl-benzonitrile

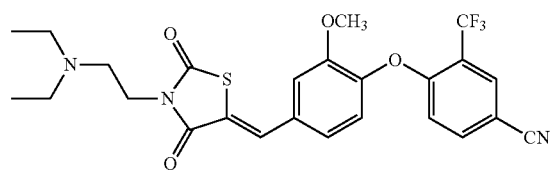 [SMILES: CCN(CC)CCN1C(=O)S/C(=C\c2ccc(Oc3ccc(C#N)cc3C(F)(F)F)c(OC)c2)C1=O]

The title compound was prepared using (2-Chloro-ethyl)-diethyl-amine as described in Example 1. $^1$H NMR (400 Hz, CDCl$_3$) δ 7.97 (s, 1H), 7.89 (s, 1H), 7.68 (dd, 1H), 7.18 (m, 3H), 6.77 (d, 1H), 3.98 (bs, 2H), 3.81 (s, 3H), 2.89 (bs, 4H), 1.61 (bs, 3H), 1.18 (bs, 5H); LC/MS (m/z) [M+1]$^+$ 520.1 (calculated for C$_{25}$H$_{25}$F$_3$N$_3$O$_4$S, 520.54).

Example 8

4-{4-[3-(2-Imidazol-1-yl-ethyl)-2,4-dioxo-thiazolidin-5-ylidenemethyl]-2-methoxy-phenoxy}-3-trifluoromethyl-benzonitrile

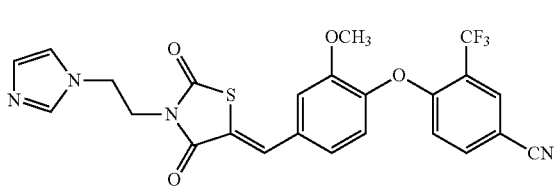 [SMILES: COc1cc(/C=C2\SC(=O)N(CCn3ccnc3)C2=O)ccc1Oc1ccc(C#N)cc1C(F)(F)F]

The title compound was prepared using 1-(2-Chloro-ethyl)-1H-imidazole as described in Example 1. $^1$H NMR (400 Hz, CDCl$_3$) δ 9.49 (bs, 1H), 7.97 (s, 1H), 7.87 (s, 1H), 7.68 (d, 1H), 7.39 (s, 1H), 7.19 (m, 4H), 6.77 (d, 1H), 4.71 (t, 2H), 4.34 (t, 2H), 3.82 (s, 3H); LC/MS (m/z) [M+1]$^+$ 515.0 (calculated for C$_{24}$H$_{18}$F$_3$N$_4$O$_4$S, 515.48).

Example 9

4-{4-[2,4-Dioxo-3-(2-piperidin-1-yl-ethyl)-thiazolidin-5-ylidenemethyl]-2-methoxy-phenoxy}-3-trifluoromethyl-benzonitrile

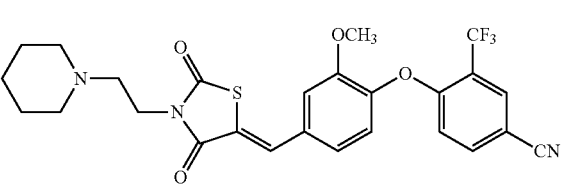 [SMILES: COc1cc(/C=C2\SC(=O)N(CCN3CCCCC3)C2=O)ccc1Oc1ccc(C#N)cc1C(F)(F)F]

The title compound was prepared as described using 1-(2-Chloro-ethyl)-piperidine in Example 1. $^1$H NMR (400 Hz, CDCl$_3$) δ 7.97 (s, 1H), 7.89 (s, 1H), 7.69 (d, 1H), 7.17 (m, 3H), 6.77 (d, 1H), 4.12 (bs, 2H). 3.81 (s, 3H), 1.62 (bs, 8H); LC/MS (m/z) [M+1]$^+$ 532.3 (calculated for C$_{26}$H$_{25}$F$_3$N$_3$O$_4$S, 532.55).

Example 10

4-{4-[2,4-Dioxo-3-(2-pyrazol-1-yl-ethyl)-thiazolidin-5-ylidenemethyl]-2-methoxy-phenoxy}-3-trifluoromethyl-benzonitrile

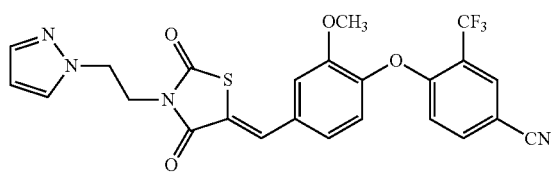 [SMILES: COc1cc(/C=C2\SC(=O)N(CCn3cccn3)C2=O)ccc1Oc1ccc(C#N)cc1C(F)(F)F]

The title compound was prepared as described using 1-(2-Chloro-ethyl)-1H-pyrazole in Example 1. $^1$H NMR (400 Hz, CDCl$_3$) δ 7.97 (s, 1H), 7.84 (s, 1H), 7.68 (dd, 1H), 7.58 (d, 1H), 7.43 (d, 1H), 7.18 (m, 3H), 6.76 (d, 1H), 6.32 (m, 1H), 4.55 (t, 2H), 4.21 (t, 2H), 3.81 (s, 3H); LC/MS (m/z) [M+1]$^+$ 515.1 (calculated for C$_{24}$H$_{18}$F$_3$N$_4$O$_4$S, 515.48).

Example 11

4-{4-[2,4-Dioxo-3-(2-[1,2,4]triazol-1-yl-ethyl)-thiazolidin-5-ylidenemethyl]-2-methoxy-phenoxy}-3-trifluoromethyl-benzonitrile

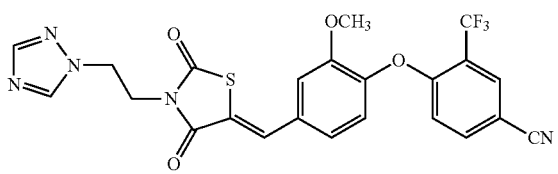 [SMILES: COc1cc(/C=C2\SC(=O)N(CCn3cncn3)C2=O)ccc1Oc1ccc(C#N)cc1C(F)(F)F]

The title compound was prepared as described using 1-(2-Chloro-ethyl)-1H-[1,2,4]triazole in Example 1. $^1$H NMR (400 Hz, CDCl$_3$) δ 8.93, 8.80 (bs, 1H), 8.13, 8.08 (s, 1H), 7.97 (s, 1H), 7.85 (s, 1H), 7.69 (dd, 1H), 7.18 (m, 3H), 6.77 (d, 1H), 4.64 (t, 1H), 4.60 (t, 1H), 4.27 (t, 1H), 3.93 (t, 1H), 3.81 (s, 3H); LC/MS (m/z) [M+1]$^+$ 516.1 (calculated for C$_{23}$H$_{17}$F$_3$N$_5$O$_4$S, 516.47).

Example 12

4-{4-[3-(2-Azepan-1-yl-ethyl)-2,4-dioxo-thiazolidin-5-ylidenemethyl]-2-methoxy-phenoxy}-3-trifluoromethyl-benzonitrile

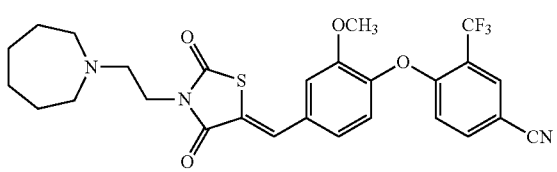 [SMILES: COc1cc(/C=C2\SC(=O)N(CCN3CCCCCC3)C2=O)ccc1Oc1ccc(C#N)cc1C(F)(F)F]

The title compound was prepared as described using 1-(2-Chloro-ethyl)-azepane in Example 1. LC/MS (m/z) [M+1]$^+$ 546.3 (calculated for C$_{27}$H$_{27}$F$_3$N$_3$O$_4$S, 546.57).

Example 13

4-{4-[2,4-Dioxo-3-(2-pyrrol-1-yl-ethyl)-thiazolidin-5-ylidenemethyl]-2-methoxy-phenoxy}-3-trifluoromethyl-benzonitrile

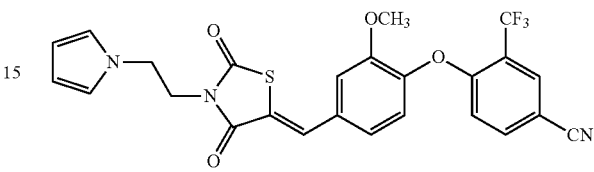

The title compound was prepared using 1-(2-Chloro-ethyl)-1H-pyrrole as described in Example 1. $^1$H NMR (400 Hz, CDCl$_3$) δ 8.32 (s, 1H), 8.01 (d, 1H), 7.93 (s, 1H), 7.51 (d, 1H), 7.36 (d, 1H), 7.26 (d, 1H), 6.91 (d, 1H), 6.66 (d, 2H), 5.93 (d, 2H), 4.17 (m, 2H), 3.94 (t, 1H), 3.85 (t, 1H), 3.75 (s, 3H); LC/MS (m/z) [M+1]$^+$ 514.1 (calculated for C$_{26}$H$_{19}$F$_3$N$_3$O$_4$S, 514.49).

Example 14

4-{4-[2,4-Dioxo-3-(2-pyrrolidin-1-yl-ethyly)-thiazolidin-5-ylidenemethyl]-2-fluoro-phenoxy}-3-trifluoromethyl-benzonitrile

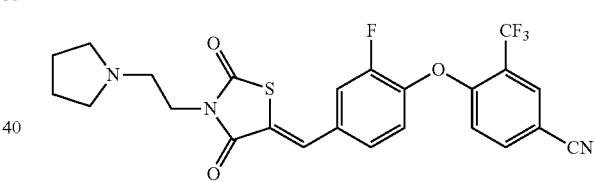

The title compound was prepared using 4-[4-(2,4-Dioxo-thiazolidin-5-ylidenemethyl)-2-fluoro-phenoxy]-3-trifluoromethyl-benzonitrile and 1-(2-Chloro-ethyl)-pyrrolidine as described in Example 1. $^1$H NMR (400 Hz, DMSO-d$_6$) δ 8.49 (s, 1H), 8.21 (dd, 1H), 8.05 (s, 1H), 7.87 (d, 1H), 7.64 (m, 2H), 7.31 (d, 1H), 3.86 (t, 2H), 2.76 (bs, 2H), 2.60 (bs, 4H), 1.73 (bs, 4H); LC/MS (m/z) [M+1]$^+$ 506.2 (calculated for C$_{24}$H$_{20}$F$_4$N$_3$O$_3$S, 506.49).

D) General Administration, Formulation, and Dosages

The present compounds are ERR-α inverse agonists and are therefore useful in treating, preventing, or inhibiting the progression of ERR-α mediated conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance and other disorders, diseases, or conditions related thereto.

The invention features a method for treating a subject with an ERR-α mediated disease, said method comprising administering to the subject a therapeutically effective amount of a pharmaceutical composition comprising a compound of the invention. In particular, the invention also provides a method for treating or inhibiting the progression of breast cancer, arthritis, inflammatory airway disease, or metabolic disorders, and associated symptoms or complications thereof in a subject, wherein the method comprises administering to the subject a therapeutically effective amount of a pharmaceutical composition comprising a compound of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

1. Dosages

Those of skill in the treatment of disorders, diseases, or conditions mediated by ERR-α can determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the ERR-α disorders described in the present invention using any of the compounds as defined herein, the dosage form will contain a pharmaceutically acceptable carrier containing between from about 0.1 mg to about 5000 mg; particularly from about 0.5 mg to about 1000 mg; and, more particularly, from about 1 mg to about 100 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as ERR-α inverse agonists is required for a subject in need thereof.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include ERR-α antagonists, glucokinase modulators, anti-diabetic agents, other lipid lowering agents, direct thrombin inhibitor (DTI), as well as lipid lowering agents such as statin drugs and the fibrates.

ERR-α antagonists include, for example, all the compounds disclosed in US-2006-0014812-A1, particularly those of the formula

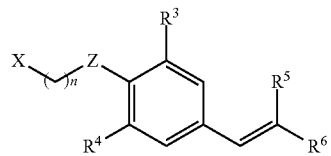

wherein:
n is 0 or 1;
Z is —O—, —S—, >NH, or >NR$^a$ where R$^a$ is alkyl, cycloalkyl, phenyl, or heterocycloalkyl;
X is an aryl or heteroaryl group;
R$^3$ is —H or —O-alkyl unsubstituted or substituted with one or more substituents independently selected from the group consisting of —OH, halo, —CN, —O-alkyl, and —N(R$^w$)R$^x$ where R$^w$ and R$^x$ are each independently —H or alkyl;
R$^4$ is selected from the group consisting of —H, halo, —O-alkyl, —CN, —NO$_2$, and —COOH; and
R$^5$ and R$^6$ are each independently —CN; —COOH; or a moiety selected from the group consisting of —COO-alkyl, —(C=O)alkyl, —(S=O)$_m$-aryl where m is 0, 1, or 2, cycloalkyl, heterocycloalkyl, —(C=O)phenyl, heteroaryl, and —(C=O)heterocycloalkyl; or R$^5$ and R$^6$ taken together with the carbon to which they are attached form an optionally benzofused heterocycloalkyl or cycloalkyl moiety;
wherein each such moiety is unsubstituted or substituted with one or more substituents independently selected from the group consisting of: —OH; =O; =S; alkyl optionally substituted with —OH, —O-alkyl, phenyl, —NH$_2$, —NH(alkyl), —N(alkyl)$_2$, halo, —CF$_3$, —COOH, or —COO-alkyl; —O-alkyl; phenyl; —O-phenyl; benzyl; —O-benzyl; cycloalkyl; —O-cycloalkyl; —CN; —NO$_2$; —N(R$^y$)R$^z$ where R$^y$ and R$^z$ are each independently —H, alkyl, or —(C=O)alkyl, or R$^y$ and R$^z$ taken together with the nitrogen to which they are attached form a heterocycloalkyl wherein one carbon ring atom is optionally replaced with >O, >NH or >N-alkyl and where one carbon ring atom is optionally substituted with —OH or =O; —(C=O)N(R$^y$)R$^z$; —(N—R$^t$)SO$_2$alkyl where R$^t$ is —H or alkyl; —(C=O) alkyl; —(S=O)$_n$)alkyl where n is 0, 1 or 2; —SO$_2$N (R$^y$)R$^z$ where R$^y$ and R$^z$ are as defined above; —SCF$_3$; halo; —CF$_3$; —OCF$_3$; —COOH; and —COOalkyl;
or a pharmaceutically acceptable salt, pharmaceutically acceptable prodrug, or pharmaceutically active metabolite of such compound.

Anti-obesity agents can be classified into several categories based upon the mechanism of action. These agents include selective serotonin reuptake inhibitors (SSRIs), serotonin agonists, serotonin and norepinephrine reuptake inhibitors, pancreatic lipase inhibitors, β3-adrenoreceptor agonists, NPY antagonists, melanocortin receptor agonists, leptin-targeted agents, CB1 antagonists (e.g. Rimonabant), monoamine reuptake inhibotors (e.g. Sibutramine), and lipase inhibitor s (e.g. Orlistat).

Serotonin agonist agents such as dexfenfluramine and fenfluramine were reported to cause cardiac valvular abnormalities when used at the prescribed dosage in combination with phentermine. Selective serotonin reuptake inhibitors (SSRIs) are generally used for the treatment of depression. These agents include fluoxetine (Prozac), paroxetine, fluvoxamine and sertraline.

Representative serotonin modulators are listed below:

(A) Selective serotonin reuptake inhibitors (SSRIs)
1. Citalopram (1-(3-(dimethylamino) propyl)-1-(4-fluorophenyl)-1,3-dihydro-5-isobenzofurancarbo nitrile, also known as citalopram hydrobromide (USAN), nitalopram, nitalapram, ZD 211, LU 10171, Lu10-171, LU 10171-B, CIPRAMIL, SEROPRAM, CIPRAM, ELOPRAM, LUPRAM, SEPRAM, PRISDAL, or CELEXA);
2. Fluoxetine (benzenepropanamine, N-Methyl-gamma-[4-(trifluoromethyl)phenoxy]-, (±) hydrochloride, also known as LY 110140, RENEURON, SARAFEM, or PROZAC);
3. Fluvoxamine (5-methoxy-1-(4-(trifluoromethyl)phenyl)-1-pentanone (E)-O-(2-aminoethyl)oxime, also known as fluvoxamine maleate (USAN), DU 23000, MK 264, SME 3110, FEVARIN, FLOXYFRAL, LUVOX, DUMYROX, DUMIROX, FLAVOXYL, FAVERIN, or DEPROMEL);
4. Indeloxazine ((+,-)-2-((indel-7-yloxy)methyl)morpholine, also known as ideloxazine, YM 08054, CI 874, ELEN, or NOIN);
5. Paroxetine hydrochloride ((3S,4R)-3-((1,3-benzodioxol-5-yloxy)methyl)-4-(4-fluorophenyl)piperidine hydrochloride, or piperidine, 3-((1,3-benzodioxol-5-yloxy)methyl)-4-(4-fluorophenyl)-, (3S-trans)-, also known as FR 7051, FG-7051, BRL 29060, BRL 29060A, NNC 207051, SI 211103, CASBOL, SEROXAT, AROPAX, PAXIL, TAGONIS, FROSINOR, DEROXAT, SEREUPIN, MOTIVAN, or PAXIL CR);
6. Sertraline (1-naphthalenamine, 4-(3,4-dichlorophenyl)-1,2,3,4-tetrahydro-N-methyl-, (1S-cis)- or 1-Naphthalenamine,4-(3,4-dichlorophenyl)-1,2,3,4-tetrahydro-N-methyl-, (1S-cis), also known as CP 51974, CP 51974 01, AREMIS, BESITRAN, GLADEM, LUSTRAL, SERAD, SERLAIN, SERLIFT, TATIG, or ZOLOFT);
7. Tianeptine (7-((3-chloro-6,11-dihydro-6-methyldibenzo (c, f) (1,2)thiazepin-11-yl)amino)heptanoic acid S,S-dioxide, also known as S 1574, or STABLON);
8. Centpropazine (1-(p-propionylphenoxy)-3-(Nsup(4)-henylpiperazynyl)-propan-2-ol);
9. Paroxetine (GEOMATRIX drug delivery system) (piperidine,3-((1,3-benzodioxol-5-yloxy)methyl)-4-(4-fluorophenyl)-, (3S-trans)-, also known as paroxetine, GEOMATRIX, PAXIL CR);
10. Escitalopram ((1S)-1-(3-(dimethylamino)propyl)-1-(4-fluorophenyl)-1,3-dihydro-5-isobenzofuran carbonitrile, or 5-Isobenzofurancarbonitrile,1-(3-(dimethylamino)propyl)-1-(4-fluorophenyl)-1,3-dihydro (S)-, also known as escitalopram, xalate (USAN), citalopram, (S)(+)-citalopram, LU 26042, LU 26054, Lu26-054, or CIPRALEX);
11. Litoxetine (4-[(2-Naphthalenyl)methoxy]piperidine, also known as SL 810385);
12. (S)-Fluoxetine ((S)—N-methyl-gamma-(4-(trifluoromethyl)phenoxy)benzenepropanamine);
13. Cericlamine ((+,-)-3,4-dichloro-beta-(dimethylamino)-beta-methylbenzenepropanol, also known as JO 1017(+,-), JO 1239(-), or JO 1240(+));
14. Dapoxetine ((+)-(S)—N,N-dimethyl-alpha-(2-(1-naphthyl-oxy)ethyl)benzylamine HCl, also known as LY-210448 or LY-243917);
15. 6-Nitroquipazine derivatives;
16. Series of substituted 6-nitroquipazines (Pharmaprojects No. 3391);
17. AAL 13 (2-(4-(3-chloropropyl)-1-piperazinyl) quinoline);
18. Depression therapy (by Vita Invest, Spain);
19. DUP 631 ($C_{13}H_{23}NO_2S$);
20. Fl 4503 (by Ferrer, Spain);
21. Series of indolylcyclohexylamines (Pharmaprojects No. 6443, American Home Products);
22. LY 280253 (N-Methyl-N3-[4-(methylthio)phenoxy)-3-phenylpropyl]amine);
23. LY 285974 (by Lilly);
24. Omiloxetine (Ethanone,2-((3R,4S)-3-((1,3-benzodioxol-5-yloxy)methyl)-4-(4-fluorophenyl)-1-piperidinyl)-1-(4-fluorophenyl)-, rel-, also known as Fl-4500, Fl-4501, Fl-4503); and
25. WF 31 (8-Methyl-2beta-propanoyl-3beta-(4-(1-methylethyl)-phenyl)-8-azabicyclo[3.2.1]);

(B) Serotonin agonists and partial agonists
1. Dexfenfluramine; and
2. Fenfluramine;

(C) Serotonin reuptake inhibitor with serotonin agonist activity
1. EMD-68843 (2-benzofurancarboxamide, 5-(4-(4-(5-cyano-1H-indol-3-yl)butyl)-1-piperazinyl)-, also known as SB-659746-A);
2. OPC-14523 (2(1H)-quinolinone, 1-(3-(4-(3-chlorophenyl)-1-piperazinyl)propyl)-3,4-dihydro-5-methoxy);
3. Vilazodone (5-{4-[4-(5-Cyano-3-indolyl)-butyl]-1-piperazinyl}-benzofuran-2-carboxamide, also known as EMD 68843 or SB 659746A);
4. Series of condensed thiazoles (3-(benzo(b)thiophen-3-yl)-5,6-dihydroimidazo (2,1-b)thiazolemonohydrobromide dihydrate, Pharmaprojects No. 5274, Abbott); and
5. VN-2222 (VN-8522, by Vita Invest, Spain).

Preferred examples of serotonin modulators include selective serotonin reuptake inhibitors such as Citalopram, Fluoxetine, Fluvoxamine, Indeloxazine, Paroxetine hydrochloride, Sertraline, Tianeptine, Centpropazine, Paroxetine, Escitalopram, and Litoxetine.

The following are also anti-obesity agents useful in the combination therapies of the present invention:

(A) Amylin and amylin analogs
1. Pramlintide (I-Lysyl-I-cysteinyl-I-asparaginyl-I-threonyl-I-alanyl-I-threonyl-I-cysteinyl-I-alanyl-I-threonyl-I-glutaminyl-I-arginyl-I-leucyl-I-alanyl-I-asparaginyl-I-phenylalanyl-I-leucyl-I-valyl-I-histidyl-I-seryl-I-seryl-I-asparaginyl-I-asparaginyl-I-phenylalanylglycyl-I-prolyl-I-isoleucyl-I-leucyl-I-prolyl-I-prolyl-I-threonyl-I-asparaginyl-I-valylglycyl-I-seryl-I-asparaginy l-I-threonyl-I-tyrosinamide cyclic (2-7)-disulfide, also known as pramlintide acetate, AC 137, ACO 137, AC 0137, SYMLIN, Tripro-amylin, or NORMYLIN);
2. Amylin agonists;
3. ACO 253 (AC 253, GG 747, GR 1150747A, or ANTAM);

(B) Ciliary neurotrophic factors (CNTF)
1. AXOKINE;
2. PEG-AXOKINE;
3. Peptide mimic of ciliary neurotrophic factor (CNTF mimic, also known as MYELOS);
4. Ciliary neurotrophic factor (CNTF by Fidia, Italy);

(C) Glucagon-like peptide—1
1. AC-2993 (also known as exendin-4, AC-2993 LAR, Medisord Exendin, AC-2993, Medisorb, or extendin-4, Amylin);
2. Exendin 4 (His-Gly-Glu-Gly-Thr-Phe-Thr-Ser-Asp-Leu-Ser-Lys-Gln-Met-Glu-Glu-Glu-Ala-V-al-Arg-Leu-Phe-Ile-Glu-Trp-Leu-Lys-Asn-Gly-Gly-Pro-Ser-Ser-Gly-Ala-Pro-Pro-Pro-Ser-amide, also known as AC 2993, AC 2993 LAR, Medisord Exendin, or AC-2993, Medisorb);
3. GLP-1 (Glucagon-like peptide-17-36 amide);
4. Glucagon-like peptide-1 oral transmucosal formulation;
5. Exendin 3 (His-Ser-Asp-Gly-Thr-Phe-Thr-Ser-Asp-Leu-Ser-Lys-Gln-Met-Glu-Glu-Glu-Ala-V-al-Arg-Leu-Phe-Ile-Glu-Trp-Leu-Lys-Asn-Gly-Gly-Pro-Ser-Ser-Gly-Ala-Pro-Pro-Pro-Ser-amide);

(D) Leptin & leptin mimetics
1. Leptin (2nd-generation);
2. Leptin agonists;
3. Leptin expression modulators;
4. Leptin signalling pathway modulators;
5. Leptin modulator;
6. Leptin (by IC Innovations, UK);
7. Leptin receptor, Monoclonal antibodies;
8. Recombinant native leptin;
9. LY-355101;
10. Leptin, Amylin (E) Melanocortin receptor agonist (MC4)
1. HP-228 (Glycinamide, N-acetyl-L-norleucyl-L-glutaminyl-L-histidyl-D-phenylalanyl-L-arginyl-D-tryptophyl-);
2. Melanocortin-4 receptor agonist (by Palatin, USA);
3. Melanocortin 4 agonist (by Pharmacopeia, Roche);
4. MC-4 agonists (by Millennium, Chiron)
5. Melanocortin-4 agonist (by Melacure Therapeutics, Sweden);
6. Melanocortin receptor modulators (Pharmaprojects No. 5224, Neurocrine Biosciences, US);
7. Pharmaprojects No. 5967, Trega/Novartis;

(F) NPY antagonists
1. AXC 0216;
2. AXC 1829;
3. SA-0204 (Neuropeptide Y antagonist, Apoptosis stimulator, Lipid metabolism modulator);
4. Alpha-trinositol (D-myo-Inositol, 1,2,6-tris(dihydrogen phosphate), also known as PP-56);
5. H 40922 (H 409/22);
6. BMS-192548 (1,11 (4H,5H)-naphthacenedione,2-acetyl-4a,12a-dihydro-3,4a,10,12,12a-pentahydroxy-8-methoxy-, TAN 1612 isomer);
7. Alanex (1,4-bis{(4-amino-6-methoxyphenylamino-1,2-dihydro-1,3,5-triazin-2-yl)-4-phenoxymethyl}benzene, Neuropeptide Y derivatives);
8. PD-160170 (6-(2-isopropyl-benzenesulfonyl)-5-nitro-quinolin-8-ylamine);
9. 2,4-Diaminopyridine derivatives (6-(5-ethyl-1,3,4-thiadiazol-2-ylthiomethyl)-4-morpholino-2-(3-(2-propenyloxycarbonylamino)benzylamino)pyridine, Pharmaprojects No. 5618, Banyu/Merck);
10. Arpromidine analogs;
11. Neuropeptide Y antagonist (Pharmaprojects No. 4990, Pfizer);
12. 4 Methyl substituted benzimidazoles (NPY-1 antagonist, NPY-2 antagonist);
13. LY-366337 (Neuropeptide Y1 antagonist);
14. S-2501, S-25579, S-25584, S-25585, S-19528, S-34354 (all Neuropeptide Y1/5 antagonists);
15. Neuropeptide Y antagonist (subtypes 1 and 5) and Galanin receptor antagonist (Pharmaprojects No. 4897, Bristol-Myers Squibb);
16. Benzylamine derivatives (1-arylpiperazinyl-1-alkyloxyphenyl-4-alkylcycloalkanes);
17. J-104870 (Neuropeptide Y1 antagonist, Appetite suppressant);
18. LY-357897 (Neuropeptide Y1 antagonist);
19. Neuropeptide Y1 antagonist (Pfizer/Neurogen);
20. SR-120107A (Neuropeptide Y1 antagonist);
21. BIBO-3304 ((R)—N-((4-(aminocarbonylaminomethyl)-phenyl)methyl)-N2-(diphenylacetyl)-argininamide trifluoroacetate);
22. BIBP 3226 ((R)—N-(4-((aminoiminomethyl)amino)-1-((((4-hydroxyphenyl)methyl)amino)carbonyl)butyl)-alpha-phenylbenzeneacetamide, or benzeneacetamide, N-((1R)-4-((aminoiminomethyl)amino)-1-((((4-hydroxyphenyl)methyl)amino)carbonyl)butyl)-alpha-phenyl-);
23. SR 120819A (benzenepropanamide, N-(1-((4-((((4-((dimethylamino)methyl)cyclohexyl)methyl)amino) iminomethyl)phenyl)methyl)-2-oxo-2-(1-pyrrolidinyl) ethyl)-alpha-((2-naphthalenylsulfonyl)amino)-, (alphaR—(N(R*(cis)),alphaR*))-);
24. NGD-95-1 (CP-422935, NGD 951);
25. Compounds with benzazepine nuclei (Neuropeptide Y1 antagonist);
26. Neuropeptide Y1 antagonist (by Yamanouchi Pharmaceutical);
27. GI-264879A (Neuropeptide Y1 antagonist);
28. GW-1229 ([2',4],[2,4']homodimer of Ile-Glu-Pro-Dpr-Tyr-Arg-Leu-Arg-Tyr-CONH2, where Dpr is diaminopropionic acid, also known as 1229U91, MN-24, GR-231118);
29. BIIE-0246 (Cyclopentaneacetamide, N-[(1S)-4-[(aminoiminomethyl)amino]-1-[[[2-(3,5-dioxo-1,2-diphenyl-1,2,4-triazolidin-4-yl)ethyl]amino]carbonyl]butyl]-1-[2-[4-(6,11-dihydro-6-oxo-5H-dibenz[b,e]azepin-11-yl)-1-piperazinyl]-2-oxoethyl]-);
30. Neuropeptide Y2 antagonist (by Neurogen, USA);
31. Amide derivatives (Neuropeptide Y5 antagonist);
32. Neuropeptide Y agonist and antagonist-subtypes 1 and 5 (Schering-Plough)
33. N-(sulfonamido)alkyl-[3a,4,5,9b-tetrahydro-1H-benzo[e]indol-2-yl]amine (RWJPRI);
34. Neuropeptide Y5 antagonist (by Novartis);
35. Neuropeptide Y5 antagonist (by Pfizer/Neurogen);
36. Pyrrolo[3,2-d]pyrimidine based neuropeptide Y5 antagonists;
37. CGP-71683 (Pharmaprojects No. 5651, CGP-71683A);
38. Neuropeptide Y5 agonist/antagonist (Pharmaprojects No. 5664, Bayer);

(G) Histamine H3 receptor antagonists
1. GT-2331 (3-((1R,2R)-2-(5,5-dimethyl-1-hexynyl)cyclopropyl)-1H-imidazole, also known as PERCEPTIN);
2. Ciproxifan (Cyclopropyl-(4-(3-1H-imidazol-4-yl)propyloxy)phenyl)methanone, also known as BP 2359 or Compound 359);

3. Compound 421 (imidazoylpropanol derivative, INSERM (France)/Bioprojet);
4. FUB 181 (3-(4-chlorophenyl)propyl-3-(1H-imidazol-4-yl) propyl ether);
5. GR 175737 (3-((4-chlorophenyl)methyl)-5-(2-(1H-imidazol-4-yl)ethyl)-1,2-oxadiazole);
6. GT 2227 (4-(6-cyclohexyl-3(Z)-hexenyl)imidazole maleate);
7. GT 2394 ((1R,2R)-(trans-2-Imidazol-4-ylcyclopropyl)-(cyclohexylmethoxy)carboxamide);
8. GT-2016 (piperidine, 1-(5-cyclohexyl-1-oxopentyl)-4-(1H-imidazol-4-yl)-);
9. Imoproxifan (1-(4-(3-(1H-imidazol-4-yl)propoxy)phenyl)ethan-1-one oxime);
10. Impentamine (by Berlin Free University);
11. Abbott Laboratories H3 antagonist for Attention deficit Hyperactivity Disorder (ADHD);
12. Gliatech (USA) H3 antagonist for eating disorder;
13. Series of novel carbamates as derivatives of 3-(1H-imidazol-4-yl)propanol with an N-alkyl chain;
14. Series of analogs with a neutral linker leading to 4-(1H-imidazol-4-ylmethyl)benzene;
15. Urea, N-4-(1H-imidazol-4-ylmethyl)phenylmethyl-N'-(3,5-dichlorophenyl)-, monohydrochloride;
16. Sch-50971 (1H-imidazole, 4-[(3R,4R)-4-methyl-3-pyrrolidinyl]-);
17. Thioperamide (N-cyclohexyl-4-(1H-imidazol-4-yl)-1-piperidinecarbothioamide, also known as MR 12842);
18. UCL-1283 (by University College London);
19. UCL-1390 (4-(3-(1H-imidazol-4-yl)propoxy)benzonitrile);
20. UCL-1409 ((phenoxyalkyl)imidazoles);
21. UCL-1972 (by University College London);
22. Verongamine (benzenepropanamide, 3-bromo-.alpha.-(hydroxyimino)-N-[2-(1H-imidazol-4-yl)ethyl]-4-methoxy-, (E)-);
23. VUF-9153 (Carbamimidothioic acid, [(4-chlorophenyl)methyl]-, 3-(1H-imidazol-4-yl)propyl ester, also known as Clobenpropit);

(H) Pancreatic lipase inhibitors
1. Orlistat (L-Leucine, N-formyl-, 1-((3-hexyl-4-oxo-2-oxetanyl)methyl)dodecyl ester, (2S-(2alpha(R*),3beta))-, or N-formyl-L-leucine (2S-(2alpha(R*),3beta))-1-((3-hexyl-4-oxo-2-oxetanyl)methyl)dodecyl ester, also known as Orlipastat, RO 180647, Tetrahydrolipstatin (THL), XENICAL, or ZENICAL);
2. ATL 962 (also known as AZM 119 or Alizyme);
3. GelTex (Anti-obesity therapeutics);
4. AZM-131 (by Yakurigaku Chuo Kenkyusho/Institute of Food Research);
5. RED 103004 (XiMed Group (United Kingdom)/Bio-Clin);

(i) Alpha melanocyte stimulating hormone analogues
1. Melanotan II (acetyl-norleucyl-aspartyl-histidyl-D-phenylalanyl-arginyl-tryptophyl-lysinamide C-4.2-N-6.7-lactam, also known as MT II);
2. MBU-23, MBU-23, MBU-24, MBU-27, MBU-28 and MBU-29 (all described in WO 009827113);
3. MSH fusion toxin (also known as DAB389MSH, anti-melanoma, chimaera)
4. SHU-9119 (L-Lysinamide, N-acetyl-L-norleucyl-L-.alpha.-aspartyl-L-histidyl-3-(2-naphthalenyl)-D-alanyl-L-arginyl-L-tryptophyl-, (2.fwdarw.7)-lactam, also known as MBX 36)
5. SHU-9005 (a substituted derivative of alpha-MSH)
6. ZYC-200 (alpha-MSH, Schepens/ZYCOS with BIOTOPE expression cassette system)

(J) Mixed serotonin reuptake inhibitor with serotonin or alpha adrenergic antagonist activity
1. Nefazodone (2-(3-(4-(3-chlorophenyl)-1-piperazinyl)propyl)-5-ethyl-2,4-dihydro-4-(2-phenoxyethyl)-3H-1,2,4-triazol-3-one, also known as MJ 13754, MS 13754, BMY 13754, BMY 137541, SERZONE, DUTONIN, RESERIL, NEFADAR, NIFEREL, MENFAZONA, RULIVAN, DEPREFAX, or SERZONIL);
2. YM 992 ((S)-2-(((7-fluoro-2,3-dihydro-1H-inden-4-yl)oxy)methyl)morpholine hydrochloride, or (S)-2-(((7-fluoro-2,3-dihydro-1H-inden-4-yl)oxy)methyl)morpholine hydrochloride, also known as YM 35992);
3. A 80426 ((R)—N-methyl-N-((1,2,3,4-tetrahydro-5-methoxy-1-naphthalenyl)methyl)-6-benzofuranethanamine);
4. 5-HT1A antagonist (by Vita-Invest, Spain);
5. Nefazodone metabolite (by Sepracor, USA);
6. Serotonin reuptake inhibitors/serotonin 1A antagonists (Wyeth-Ayerst)

(K) Appetite-suppressants acting through adrenergic mechanisms
1. benzphetamine;
2. phenmetrazine;
3. phentermine;
4. diethylpropion;
5. mazindol;
6. sibutramine;
7. phenylpropanolamine;
8. ephedrine (L) Mixed serotonin & dopamine reuptake inhibitors
1. BL-1834 (1-propanamine, 3-dibenz(b,e)oxepin-11 (6H)-ylidene-N,N-dimethyl);
2. NS-2389 or NS-2347 (GW-650250A, GW 650250);
3. (R)-Sibutramine;
4. NS-2359 (by NeuroSearch, Denmark);
5. RTI-112 or RTI-113 or RTI-177 (8-Azabicyclo(3.2.1) octane-2-carboxylic acid,3-(4-chloro-3-methylphenyl)-8-methyl-, methyl ester, hydrochloride, (1R,2S,3S,5S));
6. BSF-74681(Abbott);
7. Hyperforin trimethoxybenzoate (IDN-5491);

(M) Mixed serotonin reuptake inhibitors and dopamine antagonist
1. SLV-310 (Solvay, Belgium);
2. EMD 86006 (3-(2-(3-(4-fluorophenyl)benzylamino) ethoxy)benzonitrile);
3. SLV 301 (by Solvay);

(N) Norepinephrine & serotonin reuptake inhibitors (NSRI)
1. Milnacipran (Cyclopropanecarboxamide, 2-(aminomethyl)-N,N-diethyl-1-phenyl-, cis-(+/−)-, or (±)-cis-2-(Aminomethyl)-N-diethyl-1-phenyl cyclopropane carboxamide hydrochloride, also known as F-2207, F-2641, TN-912, DALCIPRAN, IXEL, MIDACIPRAN, MIDALCIPRAN, MILNACIPRAN SR, TOLEDOMIN);
2. Tramadol, Purdue (cyclohexanol, 2-((dimethylamino)methyl)-1-(3-methoxyphenyl)-, cis-(+/−), also known as TRAMADOL, Tramadol, CR, or Toray);
3. Milnacipran (drug delivery system, sustained release);
4. Duloxetine ((S)—N-methyl-gamma-(1-naphthalenyloxy)-2-thiophenepropanamine, or (+)-(S)—N-Methyl-gamma-(1-naphthyloxy)-2-thiophene-propylamine hydrochloride, also known as LY 248686, duloxetine oxalate, LY-223332, LY-223743, LY-223994, LY-227750, LY-227942, LY-228993, LY-248686, LY-264452, LY-264453, LY-267826"

5. Naltrexone+tramadol (morphinan-6-one,17-(cyclopropylmethyl)-4,5-epoxy-3,14-dihydroxy(5alpha)-, mixt withcyclohexanol, 2-((dimethylamino)methyl)-1-(3-methoxyphenyl)-, cis-(+/—)-, also known as PTI-601, tramadol+naltrexone, Pain T)
6. (S) sibutramine ((S)-1-(4-chlorophenyl)-N,N-dimethyl-alpha-(2-methylpropyl)cyclobutanemethanamine);
7. Tramadol, Labopharm (cyclohexanol, 2-((dimethylamino)methyl)-1-(3-methoxyphenyl)-, cis-(+/−), also known as tramadol, Contramid);
8. F 98214TA (by FAES, Spain);
9. S 33005 ((—)-1-(1-Dimethylaminomethyl-5-methoxy-benzocyclobutan-1-yl)cyclopentanol);
10. Tacrine analogues, SIDR;

(O) Serotonin, norepinephrine and dopamine reuptake inhibitors
1. Sibutramine (cyclobutanemethanamine,1-(4-chlorophenyl)-N,N-dimethyl-alpha-(2-methylpropyl)-, or 1-(4-chlorophenyl)-N,N-dimethyl-alpha-(2-methylpropyl)cyclobutanemethanamine hydrochloride monohydrate, also known as Sibutramine hydrochloride monohydrate, BTS-54354, BTS-54505, BTS-54524, KES-524, MERIDIA, REDUCTIL, RADUCTIL, REDUCTASE, PLENTY, ECTIVA);
2. Venlafaxine (cyclohexanol, 1-[2-(dimethylamino)-1-(4-methoxyphenyl)ethyl], also known as WY 45030, WY 45651, WY 45655, DOBUPAL, EFECTIN, EFEXOR, EFFEXOR, ELAFAX, VANDRAL, TREVILOR);
3. Venlafaxine XR (cyclohexanol, 1-(2-(dimethylamino)-1-(4-methoxyphenyl)ethyl)-, hydrochloride, also known as EFFEXOR XR,I EFFEXOR ER, EFFEXOR XL, EFFEXOR LP, DOBUPAL RETARD, VANDRAL RETARD, EFFEXOR-EXEL 75, EFEXOR XR, EFEXOR DEPOT, ELAFAX XR);
4. Venlafaxine (drug delivery system, OROS oral controlled release, also known as venlafaxine, OROS, or EFEXOR XR)
5. (+)-Desmethylsibutramine (also known as DDMS, Didesmethylsibutramine-Sepracor);
6. BTS-74398 (1-[1-(3,4-Dichlorophenyl)cyclobutyl]-2-(3-dimethylaminopropylthio)ethanone, Abbott Pharmaprojects No. 6247);
7. Desmethylvenlafaxine (by Sepracor);

(P) Appetite-suppressant agents acting through dopamine mechanisms
1. Apomorphine;

(Q) Selective norepinephrine (noradrenaline) reuptake inhibitors
1. Reboxetine ((2S)-rel-2-((R)-(2-ethoxyphenoxy)phenylmethyl)morpholine, or morpholine, 2-[(2-ethoxyphenoxy)phenylmethyl]-, (R,S)—, methanesulfonate, also known as reboxetine mesylate (USAN), FCE 20124, FCE 21684, PNU 155950E, EDRONAX, PROLIFT, VESTRA, IRENON, NOREBOX);
2. Tomoxetine ((gamma.R)—N-methyl-gamma-(2-methylphenoxy)benzenepropanamine, or (—)-N-Methyl-3-phenyl-3-(o-tolyloxy)-propylamine hydrochloride, also known as LY 139603, LY 135252, LY 139602);
3. Hydroxynortriptyline ((E)-10-11-dihydro-5-(3-(methylamino)propylidene)-5H-dibenzo-(a,d)cyclohepten-10-ol);
4. LY 368975 ((R)—N-Methyl-3-[2-(methylsulfanyl)phenoxy]-3-phenyl-propylamine hydrochloroide);

(R) Combined norepinephrine and dopamine reuptake inhibitors
1. Bupropion (1-(3-chlorophenyl)-2-((1,1-dimethylethyl)amino)-1-propanone, also known as bupropion hydrochloride (USAN), bupropin, amfebutamone, BW 323U, WELLBUTRIN, QUOMEM, or ZYBAN);
2. GW 320659 ((2S-(2alpha,3alpha,5alpha))-2-(3,5-difluorophenyl)-3,5-dimethyl-2-morpholinol hydrochloride, also known as 1555, 1555U88, BW 1555U88);
3. Hydroxy bupropion (also known as bupropion, R-, or R-bupropion);
4. (–) Didesmethylsibutramine (also known as (S)-didesmethylsibutramine, desmethylsibutramine, (–)-DDMS or MERIDIA (urogenital));

(S) Mixed norepinephrine reuptake inhibitor and other neurotransmitter antagonists
1. Zotepine (2-((8-chlorodibenzo(b,f)thiepin-10-yl)oxy)-N,N-dimethylethylamine, also known as LODOPIN, NIPOLEPT, ZOLEPTIL, ZOPITE, SETOUS, MAJORPIN);
2. MCI 225 (4-(2-fluorophenyl)-2-methyl-6-(piperazin-1-yl)-3a,7a-dihydrothieno(2,3-d)pyrimidine, or 4-(2-Fluorophenyl)-6-methyl-2-piperazinothieno[2,3-d]pyrimidine hydrochloride hydrate);
3. A 75200 ((R*,R*)-(+,–)-3-phenyl-1-((6,7,8,9-tetrahydronaphtho(1,2-d)-1,3-dioxol-6-yl)methyl)pyrrolidine);

(T) Combined serotonin reuptake inhibitors and sigma receptor antagonists
1. E-5296 (by Esteve, Spain);
2. E-6276 (by Esteve, Spain);
3. E-5842 (pyridine, 4-(4-fluorophenyl)-1,2,3,6-tetrahydro-1-(4-(1H-1,2,4-triazol-1-yl)butyl)-, 2-hydroxy-1,2,3-propanetricarboxylate (1:1));
4. E 5826 (citrate salt of E-5842);

(U) Other neurotransmitter modulators with serotonin or norepinephrine uptake inhibitor activity
1. Pirlindole (1H-pyrazino(3,2,1-jk)carbazole, 2,3,3a,4,5,6-hexahydro-8-methyl-, also known as CAS-125, Pyrazidol, pirazidol, LIFRIL, IMPLEMENTOR);
2. NS-2330 (by NeuroSearch, Denmark);
3. VAN-H36 (by Vita-Invest, Spain);
4. UR 1827 (2-(1-Benzylpiperidin-4-yl)-1-[4-(5-methylpyrimidin-4-ylamino)phenyl]-1-ethanone);

(V) C-75 (Fatty acid synthase inhibitor)
(W) S 15261 (L-4-(2-(2-(9-Fluorenyl)acetamido)ethyl) benzoic acid 2-(2-methoxy-2-(3-(trifluoromethyl)phenyl) ethylamino)ethyl ester)
(X) S 100B (Neurotrophic factor)
(Y) Stimulators of uncoupling protein function
(Z) Cholecystokinin agonists
(AA) Androgens
1. dehydroepiandrosterone;
2. dehydroepiandrosterone derivatives (such as etiocholandione);
(BB) Testosterone
(CC) Anabolic steroids (eg, oxandrolone)
(DD) Steroidal hormones
(EE) Amylase inhibitors
(FF) Enterostatin agonists/mimetics
(GG) Orexin/hypocretin antagonists
(HH) Urocortin antagonists
(II) Bombesin agonists
(JJ) Modulators of protein kinase A
(KK) Corticotropin-releasing factor mimetics
(LL) Cocaine- and amphetamine-regulated transcript mimetics
(MM) Calcitonin-gene related peptide mimetics
(NN) Nizatidine (Axid)

Other agents useful for the combination therapy of the present invention include glucokinase modulators include:

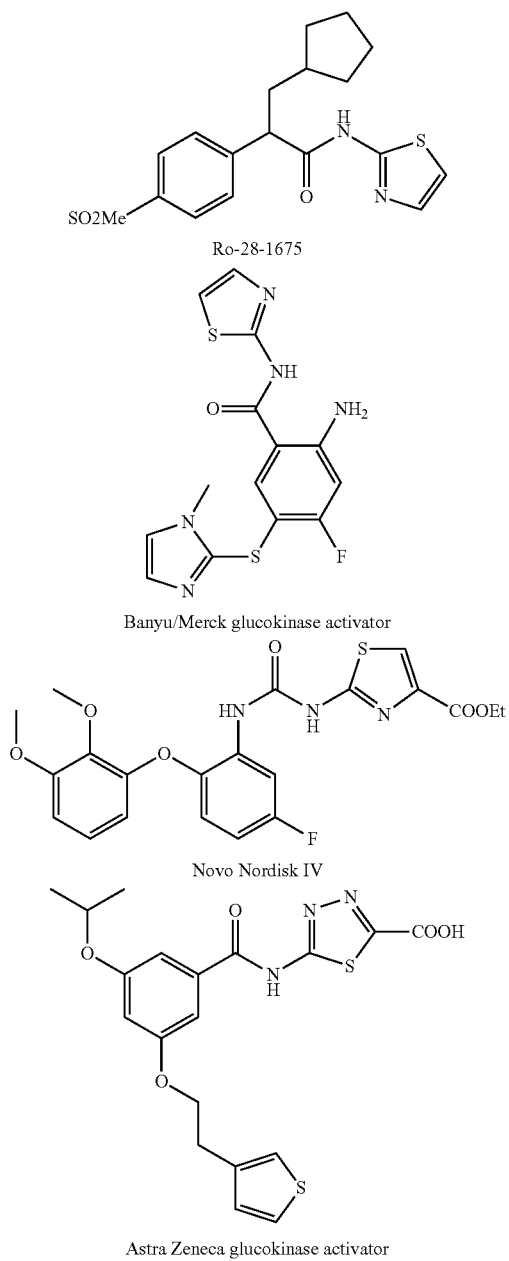

Ro-28-1675

Banyu/Merck glucokinase activator

Novo Nordisk IV

Astra Zeneca glucokinase activator

Anti-diabetic agents include RXR modulators such as:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl)nicotinic acid, known as ALRT 268 or LG 100268); and
(8) LG 100264.

Anti-diabetic agents also include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:
(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI 991, CS 045, GR 92132, GR 92132X);
(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2, 4-thiazolidinedione or 5-(6-(2-fluorobenzyloxy) naphthalen-2-ylmethyl)thiazolidine-2,4-dione, also known as MCC-555 or neoglitazone); and
(5) 5-BTZD.

Additionally, the non-thiazolidinediones that act as insulin sensitizing agents include, but are not limited to:
(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);
(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and
(3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:
(1) AD 5075;
(2) R 119702 ((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);

(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl)amino)-2-oxoethyl)-2-heptyl-4-oxo-3-thiazolidinyl)butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino)ethoxy)-alpha-(2,2,2-trifluoroethoxy)benzenepropanoic acid or 3-(4-(2-(N-(2-benzoxazolyl)-N-methylamino)ethoxy)phenyl)-2(S)-(2,2,2-trifluoroethoxy)propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl)phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:
(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl)ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis (thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo (2,1-b)oxazol-5(6H)-one);
(15) S 15261 ((−)-4-(2-((9H-fluoren-9-ylacetyl)amino)ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl)ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl)ethoxy)phenyl)-2(S)-(propylamino) propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents can further include biguanides, which decreases liver glucose production and increases the uptake of glucose. Examples of biguanides include metformin such as:
(1) 1,1-dimethylbiguanide (e.g., Metformin-DepoMed, Metformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Additionally, anti-diabetic agents include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the postprandial glucose peak. Examples of alpha-glucosidase inhibitors include, but are not limited to:
(1) acarbose (D-glucose, O-4,6-dideoxy-4-(((1S-(1alpha,4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUM IDA, or ASCAROSE);
(2) Miglitol (3,4,5-piperidinetriol, 1-(2-hydroxyethyl)-2-(hydroxymethyl)-, (2R(2alpha,3beta,4alpha,5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents can also include insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
   (4a) DPP-728 or LAF 237 (2-pyrrolidinecarbonitrile,1-(((2-((5-cyano-2-pyridinyl)amino)ethyl)amino) acetyl), known as NVP-DPP-728, DPP-728A, LAF-237);
   (4b) Sitagliptin, also known as Januvia;
   (4c) P 3298 or P32/98 (di-(3N-((2S,3S)-2-amino-3-methyl-pentanoyl)-1,3-thiazolidine)fumarate);
   (4d) TSL 225 (tryptophyl-1,2,3,4-tetrahydroisoquinoline-3-carboxylic acid);
   (4e) Valine pyrrolidide (valpyr);
   (4f) 1-aminoalkylisoquinolinone-4-carboxylates and analogues thereof;
   (4g) SDZ 272-070 (1-(L-Valyl) pyrrolidine);
   (4h) TMC-2A, TMC-2B, or TMC-2C;
   (4i) Dipeptide nitriles (2-cyanopyrrolodides);
   (4j) CD26 inhibitors; and
   (4k) SDZ 274-444;
(5) glucagon antagonists such as AY-279955; and
(6) amylin agonists which include, but are not limited to, pramlintide (AC-137, Symlin, tripro-amylin or pramlintide acetate).

Well-known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second ERR-α modulator, as described above in Sections B) and E), may also be utilized as a third antidiabetic agent, provided that it is different from the first ERR-α modulator.

F) Biological Example

TR-FRET Assay

Time-Resolved Fluorescence Resonance Energy Transfer (TR-FRET) experiments were performed to examine the functional response of ERR1 (also known as ERR-α or ERR-1) ligands. The TR-FRET assay described herein relied on the conformation of ERR1 for binding to a co-activator peptide: when a test compound binds to ERR1 and alters its conformation, it can disrupt the binding of the co-activator peptide. The components of this homogeneous secondary assay included: the $^6$His-tagged-ERR1 LBD, a GST-labeled-hSRC2 co-activator polypeptide and a fluorescent donor/acceptor pair from CIS bio international htrf/bioassays (Bedford, Mass.) using both an α-GST Europium Cryptate (Eu) label and an α$^6$His-XL665 (allophycocyanin)fluorophore.

For TR-FRET measurements, the reaction was buffered in 25 mM Tris pH 8, 2.5 mM Hepes, 20 mM KCl, 1 mM DTT, and 0.05 mg/mL BSA (-lipids). The final concentrations of reagents were 6 nM of ERR1 LBD, 6 nM GST-SRC-2 peptide, 30 nM Eu cryptate, and 7.5 nM XL665. Reactions were allowed to reach equilibrium at 25° C. for 4-18 hours before collecting data on the Analyst from LJL Biosystems (Molecular Devices Sunnyvale, Calif.). As a time-resolved method, the samples were excited at 340 nM and emission was collected for 1 ms at both 615 and 665 nm with delays of 400 and 75 μs, respectively. Dose response curves were fitted using a hyperbolic equation and the data reported is the average of 3 independent experiments.

Compounds listed in Tables II below were tested in the above assay, and they are all active modulators of ERR1.

TABLE II

| TR-FRET data | |
|---|---|
| COMPOUND # | TR-FRET EC50 (μM) |
| 1 | 0.02 |
| 2 | 0.039 |
| 3 | 0.042 |

TABLE II-continued

| TR-FRET data | |
|---|---|
| COMPOUND # | TR-FRET EC50 (μM) |
| 4 | 0.32 |
| 5 | 0.36 |
| 6 | 0.32 |
| 7 | 0.059 |
| 8 | 0.032 |
| 9 | 0.033 |
| 10 | 0.059 |
| 11 | 0.024 |
| 12 | 0.044 |
| 13 | 0.086 |
| 14 | 0.23 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method of treating a subject suffering from or diagnosed with a disease, disorder, or condition mediated by ERR-α, comprising administering to the subject a therapeutically effective amount of at least one compound of formula

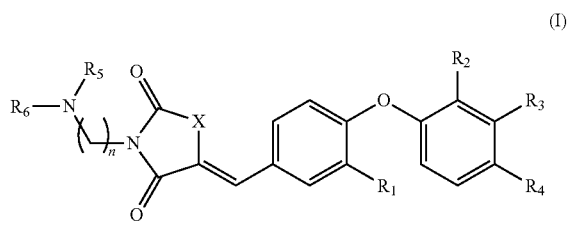

(I)

wherein

X is S or O;

n is 1-4

$R_1$ is halo, optionally substituted $C_{1-4}$alkyl, optionally substituted $C_{1-4}$alkoxy, or hydroxyl;

$R_2$ is selected from halo substituted $C_{1-3}$alkyl, cyano, halo, —C(O)NH$_2$, and —C(O)O—C$_{1-4}$alkyl, or alternatively $R_2$ is linked together to $R_3$ to form an aryl fused to the phenyl ring to which $R_2$ and $R_3$ are shown attached;

$R_3$ is H, or alternatively $R_3$ is linked together to $R_2$ to form an aryl ring fused to the phenyl ring to which $R_3$ and $R_2$ are shown attached;

$R_4$ is halo, cyano, halo substituted $C_{1-3}$alkyl, —C≡CH, —C(O)O—C$_{1-4}$alkyl, —C(O)NH$_2$, or —S(O$_2$)—C$_{1-4}$alkyl; and $R_5$ and $R_6$ are independently H or optionally substituted $C_{1-4}$alkyl, or alternatively $R_5$ and $R_6$ are linked together with the N atom to which they are attached to form an optionally substituted 5-9 membered N-containing heteroaryl or optionally substituted 5-7 membered N-containing heterocyclyl;

or an optical isomer, enantiomer, diastereomer, cis-trans isomer, racemate, or pharmaceutically acceptable salt thereof, wherein the disease, disorder, or medical condition is selected from the group consisting of obesity, diabetes, lipid disorders, artherosclerosis, hyperglycemia, elevated blood glucose level, and insulin resistance.

2. The method of claim 1, wherein the therapeutically effective amount of the compound of claim 1 is from about 0.1 mg/dose to about 5 g/dose.

3. The method of claim 2 wherein the therapeutically effective amount of the compound of claim 1 is from about 0.5 mg/dose to about 1000 mg/dose.

4. The method of claim 2 wherein the therapeutically effective amount of the compound of claim 1 is from about 1 mg/dose to about 100 mg/dose.

\* \* \* \* \*